(12) United States Patent
Bressan et al.

(10) Patent No.: US 7,186,563 B2
(45) Date of Patent: Mar. 6, 2007

(54) METHODS AND COMPOSITIONS FOR REGULATING PLANT STRESS TOLERANCE

(75) Inventors: Ray A. Bressan, West Lafayette, IN (US); Paul M. Hasegawa, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/091,100

(22) Filed: Mar. 28, 2005

(65) Prior Publication Data

US 2005/0251880 A1 Nov. 10, 2005

Related U.S. Application Data

(60) Provisional application No. 60/557,549, filed on Mar. 29, 2004.

(51) Int. Cl.
| | |
|---|---|
| A01H 5/00 | (2006.01) |
| C12N 15/82 | (2006.01) |
| C12N 15/87 | (2006.01) |
| C12N 5/14 | (2006.01) |
| C07H 21/00 | (2006.01) |

(52) U.S. Cl. ................. 435/468; 435/320.1; 435/419; 800/287; 800/289; 536/23.6

(58) Field of Classification Search .................... None
See application file for complete search history.

(56) References Cited

U.S. PATENT DOCUMENTS

2003/0233680 A1 12/2003 Thomashow et al.
2004/0019927 A1 1/2004 Sherman et al.

FOREIGN PATENT DOCUMENTS

EP 1033405 A2 * 9/2000

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Rounsley et al. (NCBI, GenBank, Sequence Accession No. AC005560, pp. 1-42, Published Mar. 11, 2002).*
Valvekens et al. (PNAS, 85:5536-5540, 1988).*
Liu et al. (Eur. J. Biochem., 262:247-257, 1999).*
"An *Arabidopsis* homeodomain transcript factor gene, *HOS9*, mediates cold tolerance through a CBF-independent pathway," by Zuh et al.; PNAS, Jun. 29, 2004, vol. 101, No. 26; pp. 9873-9878.
Chinnusamy, V., Ohta, M., Kanrar, S., Lee, B.-H., Hong, X., Agarwal, M. & Zhu, J.-K. (2003) Genes Dev. 17, 1043-1054.
Fowler, S. & Thomashow, M. F. (2002) Plant Cell 14, 1675-1690.
Gilmour, S. J., Zarka, D. G., Stockinger, E. J., Salazar, M. P., Houghton, J. M. & Thomashow, M. F. (1998) Plant J. 16, 433-442.
Guo, Y., Xiong, L., Ishitani, M. & Zhu, J.-K. (2002) Proc. Natl. Acad. Sci. USA 99, 7786-7791.
Haake, V., Cook, D., Riechmann, J. L., Pineda, O., Thomashow, M. F. & Zhang, J. Z. (2002) Plant Physiol. 130, 639-648.
Ishitani, M., Xiong, L., Stevenson, B. & Zhu, J.-K. (1997) Plant Cell 9, 1935-1949.
Ishitani, M., Xiong, L., Lee, H., Stevenson, B. & Zhu, J.-K. (1998) Plant Cell 10, 1151-1161.
Kim, J. C., Lee, S. H., Cheong, Y. H., Yoo, C.-M., Lee, S. I., Chun, H. J., Yun, D.-J., Hong, J. C., Lee, S. Y., Lim, C. O., et al. (2001) Plant J. 25, 247-259.
Knight, H., Veale, E. L., Warren, G. J. & Knight, M. R. (1999) Plant Cell 11, 875-886.
Kreps, J. A., Wu, Y, Chang, H. S., Zhu, T., Wang, X., Harper, J. F. (2002) Plant Physiol. 130, 2129-2141.
Lee, H., Xiong, L., Gong, Z., Ishitani, M., Stevenson, B. & Zhu, J.-K. (2001) Genes Dev. 15, 912-924.
Lee, B.-H., Lee, H., Xiong, L. & Zhu, J.-K. (2002) Plant Cell 14, 1235-1251.
Liu, Q., Kasuga, M., Sakuma, Y., Abe, H., Miura, S., Yamaguchi-Shinozaki, K. & Shinozaki, K. (1998) Plant Cell 10, 1391-1406.
Medina, J., Bargues, M., Terol, J., Perez-Alonso, M. & Salinas, J. (1999) Plant Physiol. 119, 463-469.
Seki, M., Narusaka, M., Ishida, J., Nanjo, T., Fujita, M., Oono, Y., Kamiya, A., Nakajima, M., Enju, A., Sakurai, T., et al. (2002) Plant J. 31, 279-292.
Thomashow, M. F. (1998) Plant Physiol. 118, 1-8.
Xin, Z. & Browse, J. (1998) Proc. Natl. Acad. Sci. USA 95, 7799-7804.
Xiong, L., Ishitani, M., Lee, H. & Zhu, J.-K. (2001) Plant Cell 13, 2063-2083.
Yamaguchi-Shinozaki, K. & Shinozaki, K. (1994) Plant Cell 6, 251-264.
Zhu, J., Gong, Z., Zhang, C., Song, C.-P., Damsz, B., Inan, G., Koiwa, H., Zhu, J.-K., Hasegawa, P. M. & Bressan, R. A. (2002) Plant Cell 14, 3009-3028.

* cited by examiner

*Primary Examiner*—Phuong T Bui
*Assistant Examiner*—Vinod Kumar
(74) *Attorney, Agent, or Firm*—Bose McKinney & Evans LLP

(57) ABSTRACT

Methods and compositions relate to improving stress tolerance in plants including cold tolerance. HOS9 is a homeobox transcription factor that controls stress tolerance in plants by modulating the activity of a number of cold-responsive genes. Transgenic plant, cell, seed and expression vectors that include a molecule having a nucleic acid sequence derived from HOS9 confer or improve cold tolerance.

4 Claims, 6 Drawing Sheets

METHODS AND COMPOSITIONS FOR REGULATING PLANT STRESS TOLERANCE

This application claims priority to U.S. provisional 60/557,549 filed Mar. 29, 2004, incorporated herein by reference.

The U.S. Government may have certain rights in this invention pursuant to National Science Foundation Grant No. 0223905-DBI.

BACKGROUND

Methods and compositions to improve stress tolerance in plants include expression of a transcription factor that improves stress tolerance in plants.

Plants exhibit many physiological and biochemical changes when exposed to low temperature and during the process of cold acclimation, which in some plants, leads to the development of freezing tolerance. Survival of these tolerant plants at freezing temperatures depends on the modulation (upregulation or down-regulation) of specific sets of genes that are associated with the development of freezing tolerance.

The molecular mechanisms governing gene expression at low temperatures are not well understood. There is little information regarding the downstream signaling components leading to the transcriptional activation of specific sets of genes in response to low temperatures. Chilling and freezing temperatures affect the productivity and quality of plants including crop plants. Understanding of cold stress signaling has scientific and agricultural significance. Molecular and genetic studies have shown that many cold responsive genes are regulated through the CRT/DRE binding factor (CBF) family of transcriptional activators that bind the CRT/DRE promoter element (C-repeat/dehydration responsive element). Overexpression of CBF/DREB1 activates the transcription of some of the target genes and also increased tolerance of the transgenic plants to various stress responses.

After a period of low-temperature exposure, plants are able to better tolerate freezing temperatures (sustain less injury), a phenomenon referred to as cold acclimation. Part of the acclimation process involves the accumulation of gene transcripts via cold perception and signal transduction leading to promoter activation of target genes. One class of these target genes includes those encoding late-embryo abundant transcripts that contain in their promoters a C repeat (CRT)/dehydration responsive element (DRE). This element confers responsiveness to cold, desiccation, and salinity. The hormone abscisic acid (ABA) also can activate some genes responsive to cold that are in this class, such as the RD29A (COR78/LT178) gene. The RD29A gene contains both CRT/DRE and the ABA responsive element. Activation of RD29A can occur through the binding of transcription factors from the ethylene responsive element-binding protein/Apetala2 family. Specifically, the CRT/DRE-binding factor (CBF)1-4 transcription factors recognize the CRT/DRE and participate in adaptive (acclimating) responses to either cold (CBF1-3) or desiccation (CBF4). Ectopic overexpression of some CBF genes results in both activation of target genes and enhanced freezing, salt, or desiccation tolerance of transgenic plants. CBF transcription factor genes themselves are activated by stress, and a MYC-type transcription factor binds to and controls the activity of the CBF3 promoter in response to stress.

It is possible that other signal pathways in addition to those mediated by CBF transcription factors are also involved in stress-adaptive responses, including cold acclimation. For instance, the eskimo1 mutant is constitutively freezing tolerant and therefore does not require signaling through the cold-activated CBF factors. Also microarray transcript analysis experiments have shown that not all cold stress-responsive target genes contain CRT/DRE or are under the control of the CBF family. In addition, constitutive expression of the normally cold-induced CBF genes does not lead to full cold acclimation of *Arabidopsis* plants.

It is possible that other upstream signal components bypass CBF activators. Signal components that mediate cold tolerance and have little or no effect on CBF gene expression could act through such an alternative pathway or might modify CBF activity itself. Until now, no specific gene product has been to shown to act independently of CBF transcription in stress-mediated signaling response in plants.

Isolation and identification of genes that control cold or freezing tolerance by activating multiple genes are desired.

SUMMARY

Methods and compositions relate to improving or conferring stress tolerance including cold tolerance in plants. Transgenic plants, cells and seeds exhibit improved cold tolerance.

An *Arabidopsis* homeodomain transcription factor localized to the nucleus mediates cold tolerance through a C repeat (CRT)/dehydration responsive element (DRE) binding factor (CBF)-independent pathway.

An *Arabidopsis* mutant hos9-1 (high expression of osmotically responsive genes) displays several altered phenotypic features, including increased sensitivity to freezing stress. The hos9-1 mutation occurs in a homeodomain transcription factor gene that affects gene expression and freezing tolerance without altering the expression of CBF genes. Mutation of HOS9 also alters several developmental characteristics including growth rate, flowering time, and trichome density. HOS9 controls freezing tolerance through a constitutive signaling pathway that is separate and distinct from the CBF regulon.

A method for conferring or improving stress tolerance in a plant includes the steps of:
(a) obtaining a nucleic acid molecule that includes a nucleotide sequence selected from the group consisting of: (i) a nucleotide sequence comprising the sequence set forth in SEQ ID NO: 1; (ii) a nucleotide sequence that includes at least 50 contiguous nucleotides of the sequence of SEQ ID NO: 1 wherein said nucleotide sequence encodes a protein that regulates a stress responsive gene; (iii) a nucleotide sequence encoding an amino acid sequence of SEQ ID NO: 2; and (iv) a nucleotide sequence having at least 70% sequence identity to the sequence of SEQ ID NO: 1; and
(b) transforming a plant with nucleic acid molecule of (a) operably linked to a promoter to produce a transgenic plant with conferred or improved stress tolerance.

The stress tolerance includes cold tolerance and the plant includes a monocot plant. The plant is a crop plant selected from a group that includes wheat, corn, peanut, cotton, oat, tomato, rice, and soybean plants.

The promoter is selected from a group that includes a viral coat protein promoter, a tissue-specific promoter, a monocot promoter, a ubiquitin promoter, a CaMV 35S promoter, a CaMV 19S promoter, a nos promoter, an Adh promoter, a sucrose synthase promoter, a tubulin promoter, a napin promoter, an actin promoter, a cab promoter, a PEPCase promoter, a 7S-alpha-conglycinin promoter, an R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a PM, promoter, a root-cell promoter, an ABA-inducible promoter, a turgor-inducible promoter, and a super promoter.

The transgenic plant is obtained through a method of transformation selected from a group that includes *Agrobacterium*-mediated, particle bombardment, electroporation, and chemical methods or any other means known to those of skill in the art. In an embodiment, the transgenic plant is stably transformed.

The stress tolerance response is mediated through genes that function independent of C repeat (CRT)/dehydration responsive element (DRE) binding factor (CBF). HOS9 may regulate some genes that are also regulated by CBF. Generally, the term "independent of CBF" means that a substantial portion of genes regulated by HOS9 are not regulated by CBF to a significant extent under the conditions used.

A method for conferring or improving stress tolerance in a plant includes transforming a transgenic plant that has SEQ ID NO: 1 or a fragment thereof with a nucleic acid molecule encoding a peptide designated C repeat (CRT)/dehydration responsive element (DRE) binding factor (CBF) or a fragment thereof.

The cold tolerance is in response to cold temperatures that range of about −20° C. to about +10° C. or in the range of about −10° C. to about +4° C. In an embodiment. the cold tolerance is achieved after cold acclimation.

An isolated recombinant expression vector includes a promoter functional in a plant cell operably linked to an isolated nucleic acid molecule encoding SEQ ID NO: 2, wherein expression of the nucleic acid molecule in a plant cell results in the plant cell's increased tolerance to an environmental stress as compared to a wild type plant cell, and wherein the environmental stress is cold and freezing temperature.

The promoter in the expression vector is selected from a group that includes a viral coat protein promoter, a tissue-specific promoter, a monocot promoter, a ubiquitin promoter, a CaMV 35S promoter, a CaMV 19S promoter, a nos promoter, an Adh promoter, a sucrose synthase promoter, a tubulin promoter, a napin promoter, an actin promoter, a cab promoter, a PEPCase promoter, a 7S-alpha-conglycinin promoter, an R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a PM, promoter, a root-cell promoter, an ABA-inducible promoter or a turgor-inducible promoter.

A promoter and a molecule with the nucleic acid sequence as set forth in SEQ ID NO: 1 include an expression cassette. The nucleic acid sequence is operably linked to the promoter in the expression cassette.

A method of producing a transgenic plant comprising a nucleic acid molecule encoding a polypeptide substantially similar to the polypeptide as set forth in SEQ ID NO: 2 includes the steps of:
 (a) transforming a plant cell with an expression vector disclosed herein; and
 (b) obtaining a transgenic plant from the plant cell that expresses the polypeptide.

A method of modulating the expression of a plurality of plant stress-related genes includes the steps of:

(a) transforming a plant cell with a nucleic acid molecule that includes a nucleotide sequence selected from the group consisting of: (i) a nucleotide sequence that includes the sequence set forth in SEQ ID NO: 1; (ii) a nucleotide sequence that includes at least 50 contiguous nucleotides of the sequence of SEQ ID NO: 1 wherein said nucleotide sequence encodes a protein that regulates a stress responsive gene; (iii) a nucleotide sequence encoding an amino acid sequence of SEQ ID NO: 2; and (iv) a nucleotide sequence having at least 70% sequence identity to the sequence of SEQ ID NO: 1; and
 (b) obtaining a transgenic plant, wherein the expression of the stress-related genes are modulated compared to wild-type plants.

The stress-related genes are selected from a group of genes listed in TABLES 1–3. Some of these stress-related genes are designated by a gene identification number selected from a group that includes At2g46400, At2g32210, and At5g44420.

Some of these stress-related genes are regulated independent of C repeat (CRT)/dehydration responsive element (DRE) binding factor (CBF).

A transgenic plant transformed with a nucleic acid molecule encoding a peptide, wherein the peptide is substantially similar to the peptide designated by SEQ ID NO: 2 or a portion thereof, such that an increased level of the peptide improves cold tolerance to the transgenic plant compared to a wild-type plant.

A seed produced by the plant disclosed herein, wherein the seed includes a nucleic acid molecule that includes a sequence substantially similar to the sequence set forth in SEQ ID NO: 1.

A transgenic plant cell that includes a nucleic acid sequence substantially similar to the nucleic acid sequence as set forth in SEQ ID NO: 1 or a fragment thereof, operably linked to a promoter, wherein expression of the nucleic acid molecule confers increases cold tolerance as compared to a wild-type plant cell.

A method of conditioning plants to cold stress by activating stress-related genes, includes the steps:
 (a) transforming a plant cell with a nucleic acid molecule comprising a nucleotide sequence selected from the group consisting of: (i) a nucleotide sequence that includes the sequence set forth in SEQ ID NO: 1; (ii) a nucleotide sequence that includes at least 50 contiguous nucleotides of the sequence of SEQ ID NO: 1 wherein said nucleotide sequence encodes a protein that regulates a stress responsive gene; (iii) a nucleotide sequence encoding an amino acid sequence of SEQ ID NO: 2; and (iv) a nucleotide sequence having at least 70% sequence identity to the sequence of SEQ ID NO: 1; and
 (b) obtaining a transgenic plant, wherein the activation of stress-related genes condition the transgenic plant compared to a wild-type plant.

A method of identifying HOS9-regulated genes in plants includes the steps of:
 (a) transforming a plant cell with a nucleic acid molecule comprising a nucleotide sequence selected from the group consisting of: (i) a nucleotide sequence comprising the sequence set forth in SEQ ID NO: 1; (ii) a nucleotide sequence comprising at least 50 contiguous nucleotides of the sequence of SEQ ID NO: 1 wherein said nucleotide sequence encodes a protein that regulates a stress responsive gene; (iii) a nucleotide sequence encoding an amino acid sequence of SEQ ID NO: 2; and (iv) a nucleotide sequence having at least 70% sequence identity to the sequence of SEQ ID NO: 1;

(b) obtaining a transgenic plant expressing the nucleic acid molecule;

(c) performing gene expression analysis; and (d) determining HOS9-regulated genes based on differences in gene expression in the transformed plants compared to wild-type plants.

The gene expression analysis is performed after exposure to cold stress and gene expreession analysis is performed using a microarray.

Identification HOS9-regulated genes in plants is also performed on a hos9 mutant or in a plant that does not express HOS9 or expresses it to a low level. For example, transgenic plants in which HOS9 transcript level or protein amount is reduced due to a mutation in the HOS9 gene or through anti-sense expression or through small interfering RNA (siRNA) method is suitable for identifying HOS9-regulated genes.

DETAILED DESCRIPTION

Figure 1:
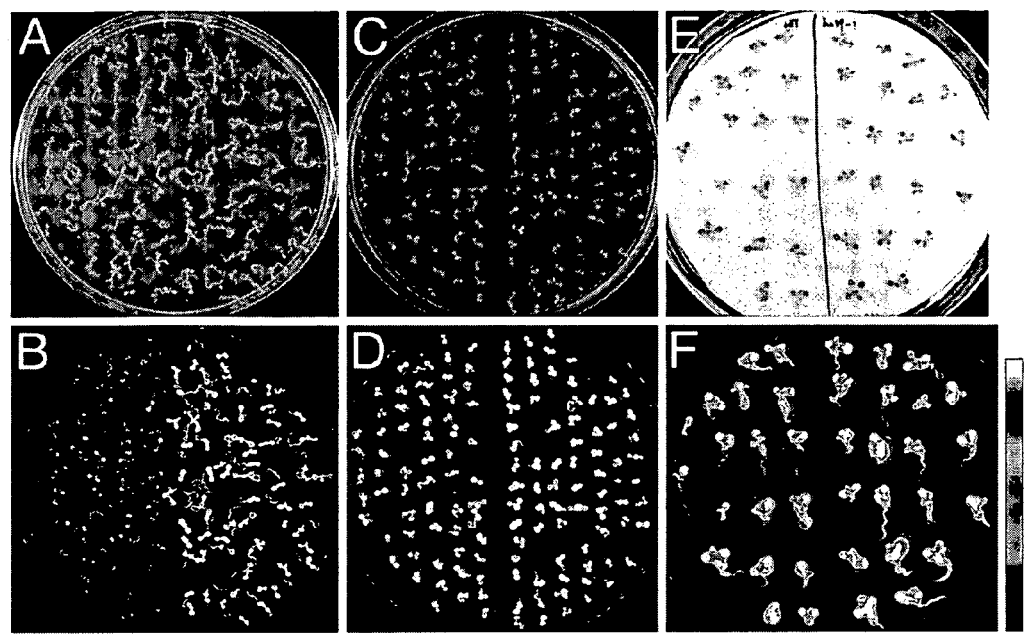
FIG. 1 shows the the RD29A::LUC expression being hyperinduced in hos9-1 mutant plants in response to low temperature. RD29A::LUC expression was quantitatively measured as luminescence intensity (counts/seedling). The scale bar at the right shows the luminescence intensity from dark color (lowest) to white (highest). (A) Wild-type (on the left) and hos9-1 (on the right) seedlings grown on an agar plate. (B) Luminescence of A after low-temperature treatment at 0° C. for 24 h. (C) Wild-type (on the left) and hos9-1 (on the right) seedlings grown on an agar plate. (D) Luminescence of C after treatment with 100 μM ABA for 3 h. (E) Wild-type (on the left) and hos9-1 (on the right) seedlings on filter paper saturated with 300 mM NaCl. (F) Luminescence of E after treatment with 300 mM NaCl for 4 h. (G) Quantification of the luminescence intensity in B (Cold), D (ABA), and F (NaCl). Also shown are data for untreated plants (Control). (H) Time course of RD29A::LUC expression in hos9-1 and wild-type plants in response to low temperature (0° C.). Bars (G and H) represent standard deviation (n=20).
Figure 1:
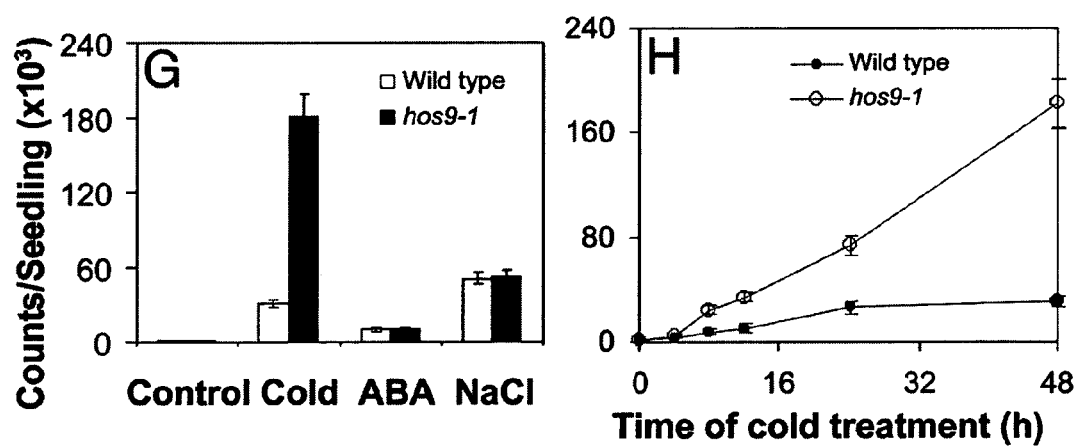

Methods to confer or improve or increase stress tolerance in particular freezing or cold tolerance in plants are disclosed. These methods include providing an increased level of HOS9 protein or a polypeptide that is substantially similar either structurally or functionally to modulate (up-regulate or down-regulate) one or more downstream target genes. For example, an increased level of the of HOS9 protein or a substantially similar peptide is provided by overexpressing a cDNA that encodes HOS9 or any nucleotide sequence capable of encoding HOS9 or a fragment thereof or a peptide that is substantially similar to HOS9. By "modulating" herein is intended to mean either up or down regulation in the expression level or an increase or decrease in the protein level or a change in the post-translational state of a protein of interest (e.g., phosphorylation, glycosylation).

Methods and compositions of the present disclosure also relate to recombinant cells, plants and plant materials (e.g., plant tissue, seeds) into which one or more gene sequences encoding a transcription regulating protein or a peptide have been introduced. A gene sequence such as SEQ ID NO: 1 or a fragment or a segment or a portion thereof encoding a transcription regulating protein is transformed into a plant or a plant cell. The transcription regulating protein such as HOS9 or SEQ ID NO: 2 or a segment or a fragment or a portion or a domain thereof is expressed within the plant which regulates expression of one or more stress tolerance genes in the plant. Some of the stress tolerance genes or those affected by HOS9 are listed in Tables 1–3. Regulation or modulation of expression may include causing one or more stress tolerance genes to be expressed under different conditions than those genes would be in the plant's native state, increasing a level of expression of one or more stress tolerance genes, and/or causing the expression of one or more stress tolerance genes to be inducible by an exogenous agent. Expression of the transcription regulating protein may be under the control of a variety of promoters.

Methods and compositions of the present disclosure also relate to cells, recombinant plants and plant materials into which a recombinant promoter is introduced which controls a level of expression of one or more gene sequences encoding a transcription regulating protein such as HOS9 or its homolog. The one or more gene sequences may be recombinant, native or non-native sequences or may be native, non-recombinant gene sequences whose expression is altered by the introduction of the recombinant promoter. A recombinant activator sequence can also be introduced to enhance the expression of endogenous HOS9 nucleic acid sequence.

Methods and compositions of the present disclosure also relate to DNA and RNA constructs, such as plasmids, vectors, and the like, that are capable of transforming a plant to confer cold tolerance. The constructs include a sequence that encodes a transcription regulating protein capable of selectively binding to a DNA regulatory sequence that regulates the one or more environmental stress tolerance genes. The binding protein such as HOS9 is preferably able to regulate expression of one or more environmental stress tolerance genes in a plant by selectively binding to the DNA regulatory sequence. When transformed into a plant, the sequence regulates expression of one or more environmental stress tolerance genes in the plant by expressing the binding protein. A variety of promoters may be used to select the degree of expression or conditions under which the regulatory gene (HOS9 or its homolog or a substantially similar protein) is expressed. For example, the promoter causes overexpression of the regulatory gene, expression of the regulatory gene independent of an environmental stress, expression of the regulatory gene at a higher level in response to the same environmental stress than would a plant in its native state, expression of the regulatory gene in response to different environmental stress conditions, and/or induction of expression of the regulatory gene by an exogenous agent to which the plant can be exposed.

An *Arabidopsis* mutant hos9-1 (high expression of osmotically responsive genes) displays several altered phenotypic features, including increased sensitivity to freezing stress. The hos9-1 mutation occurs in a homeodomain transcription factor gene (HOS9) that affects gene expression and freezing tolerance without modulating the expression of CBF genes. The mutation of HOS9 also alters several developmental characteristics including growth rate, flowering time, and trichome density. These results indicate that HOS9 controls freezing tolerance through a constitutive pathway that operates separately from the CBF regulon.

Figure 2:
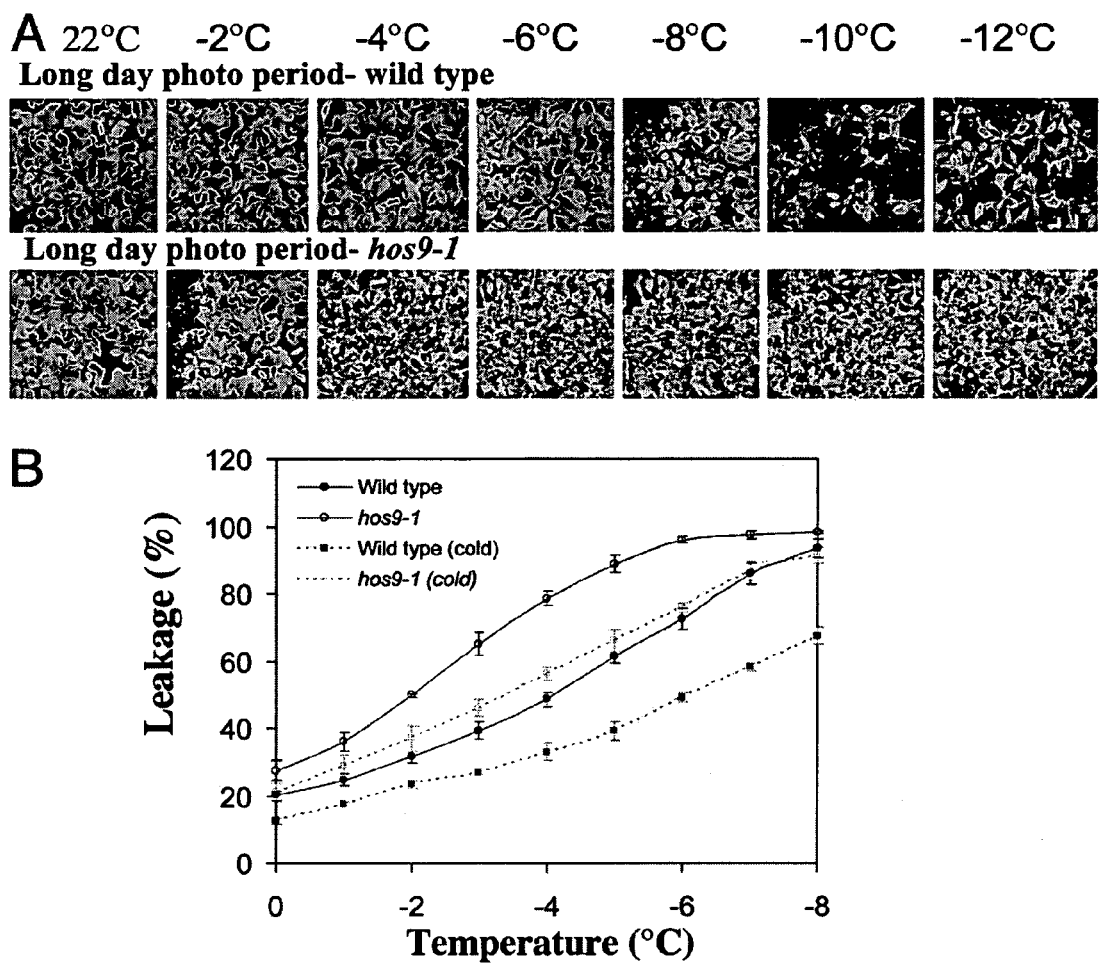
FIG. 2 shows the freezing sensitivity of hos9-1 plants. (A) Tolerance of hos9-1 plants at different temperatures below freezing under long-day photoperiod. The photographs were taken 10 d after freezing treatments. (B) Leakage of electrolytes in hos9-1 and wild-type plants when treated at temperatures below freezing. Wild-type (cold) and hos9-1 (cold), cold-acclimated wild-type, and hos9-1 plants, respectively. Bars are standard deviation (n=8).
Figure 3:
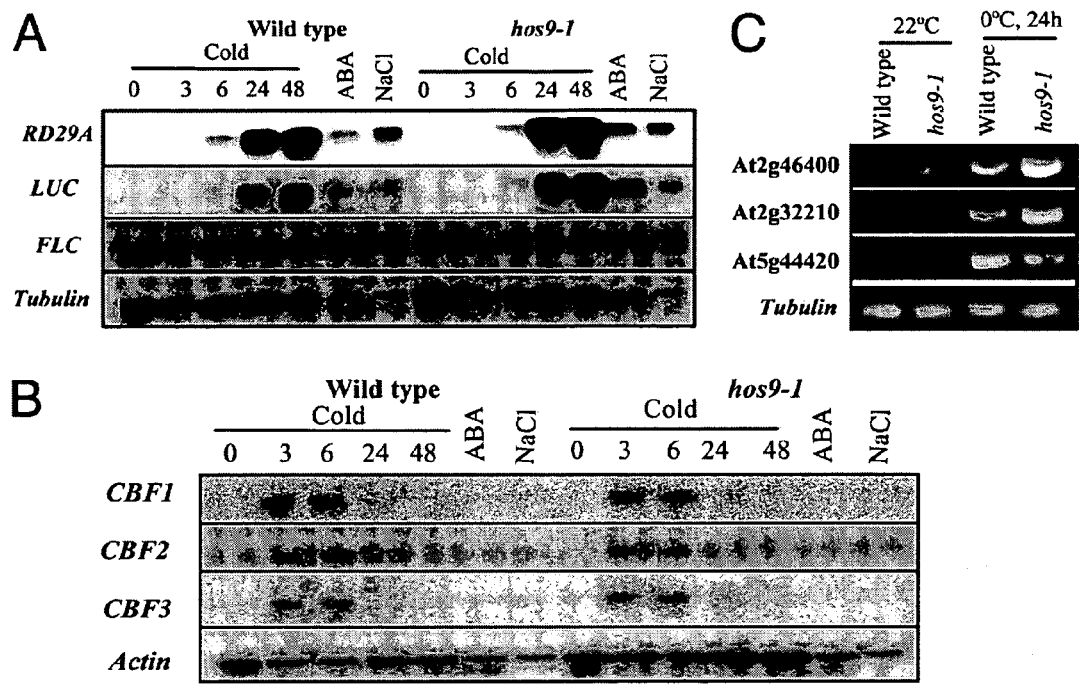
FIG. 3 shows gene regulation in hos9-1 and wild-type plants. (A) Expression of stress-responsive gene in hos9-1 and wild-type plants. Plants were subjected to low temperature (0° C.) for the indicated time periods (h). ABA, 100 μM, for 3 h; NaCl, 300 mM, for 4 h. Tubulin gene was used as loading control. (B) Steady-state transcript levels of CBF genes in hos9-1 and wild-type plants. The plants were subjected to the same treatments as stated in A. An actin gene was used as loading control. (C) RT-PCR analysis of three of the genes that were tested in the microarray analysis. The two cold-stimulated genes with higher expression in the hos9-1 than wild type in the microarray analysis encode a WRKY family transcription factor (At2g46400) and an expressed protein (At2g32210). The hos9-1 target gene with lower expression than wild type in the microarray analysis encodes a plant defensin protein (At5g44420). The tubulin gene was used as a loading control.
Figure 4:
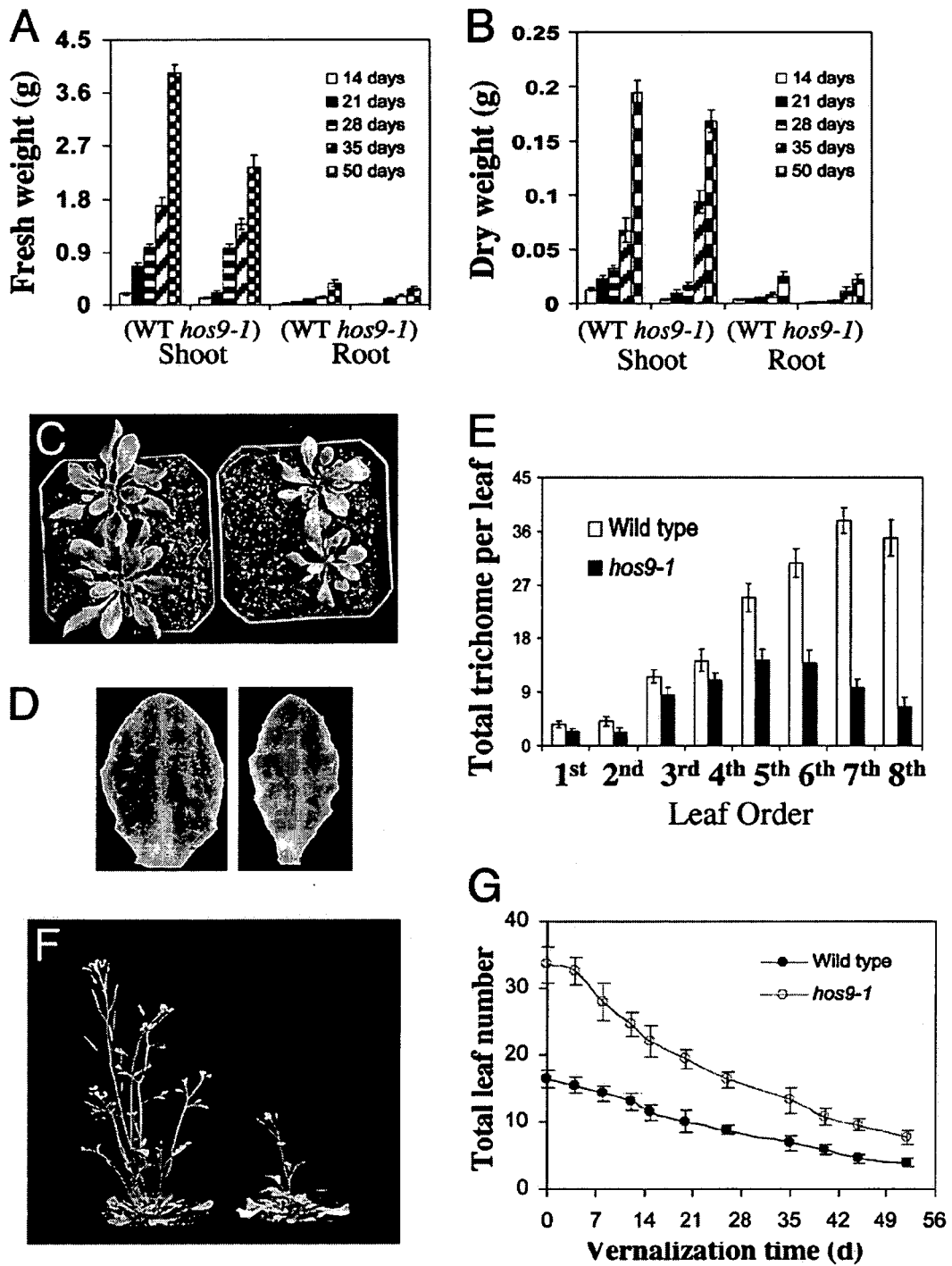
FIG. 4 shows the growth defects of hos9-1 plants. (A and B) The plant growth as indicated by shoot and root fresh and dry weights. Shoots or roots were separated from wild-type and hos9-1 plants grown in soil under long-day photoperiod at indicated developmental stages. The fresh weight of shoot or root was determined, and the samples were then dried in an oven at 65° C. for 48 h and dry weight was measured. Bars represent standard deviation (n=15). (C) Three-week-old of wild-type (Left) and hos9-1 (Right) plants grown under long-day photoperiod. (D) Trichomes on the fifth leaf of the wild-type (Left) and the hos9-1 (Right) plants. (E) Quantification of trichome numbers on rosette leaves of wild-type and hos9-1 plants. The number of trichome on different leaves was counted on a Nikon Optiphot microscope (Nikon). Bars represent standard deviation (n=20). (F) hos9-1 plant (Right) flowers later than wild-type plant (Left) under normal conditions (16 h light/8 h dark). (G) Vernalization responses of wild-type and hos9-1 plants (as indicated by flowering time/total leaf number at flowering) under long-day photoperiod. Bars represent standard deviation (n=20).

A large-scale stress response screen using *Arabidopsis* plants carrying the firefly luciferase reporter gene under the control of the stress-responsive RD29A promoter was performed. In this genetic screen *Arabidopsis* plants (*Arabidopsis* thaliana C24) homozygous for the chimeric RD29A::LUC reporter gene were mutagenized by TDNA insertion mutagenesis. The T2 population was screened for de-regulated expression of RD29::LUC by monitoring the level of cold stress inducible bioluminescence with a low light imaging system. This screen resulted in the identification and characterization of a mutant, hos9-1 (for high expression of osmotically responsive genes), in which the reporter construct was hyperactivated by low temperature, but not by abscisic acid or salinity stress (FIGS. 1 and 2). The hos9-1 mutants grew more slowly, and exhibited delayed flowering compared to wild-type plants and were more sensitive to freezing, both before and after acclimation, than the wild-type plants (FIGS. 3–4).

Figure 5:
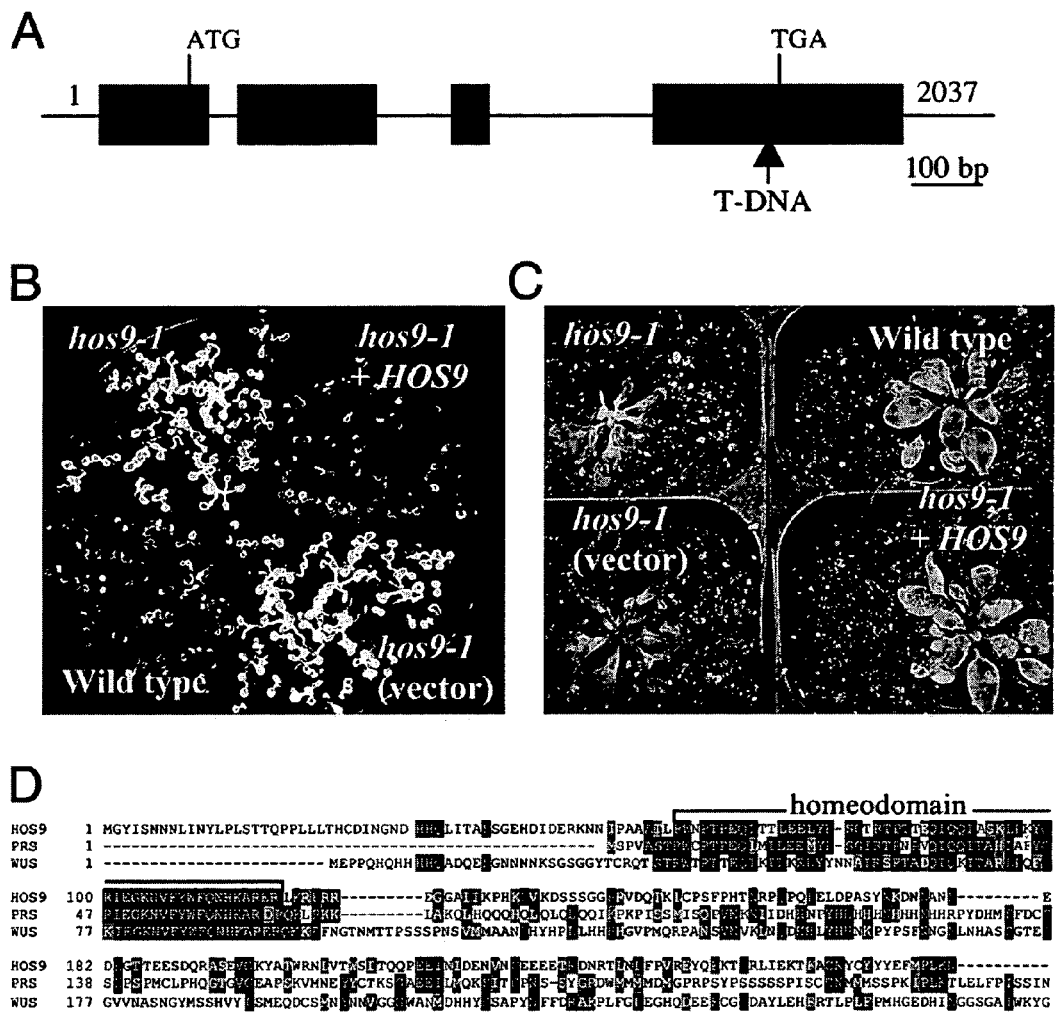
FIG. 5 illustrates that HOS9 encodes a putative homeobox protein. (A) The structure of HOS9 gene and the position of the T-DNA insert in hos9-1 mutant genome. Positions are relative to the transcription start site. Filled boxes represent exons and lines between filled boxes represent introns. (B) Luminescence image after low-temperature treatment (0° C. for 48 h) of wild-type, hos9-1, and hos9-1 transformed with pCAMBIA1200 empty vector (hos9-1 vector) and hos9-1 transformed with pCAMBIA1200 containing the HOS9 genomic fragment (hos9-1 +HOS9). The plants were grown on an agar plate. (C) Freezing tolerance of 1-mo-old plants shown in B. The treatment was done at −5° C. for 5 h, and the photograph was taken 7 d after treatment. (D) Comparison of HOS9 with its homologs. Compared proteins are: HOS9 (SEQ ID NO: 17) (AAC67326, GenBank) from *Arabidopsis*; PRS (SEQ ID NO: 15)(PRESSED FLOWER, BAB79446 (GenBank) from *Arabidopsis*; WUS (SEQ ID NO: 16)(WUCHEL, CAA09986 (GenBank) from *Arabidopsis*.
Figure 6:
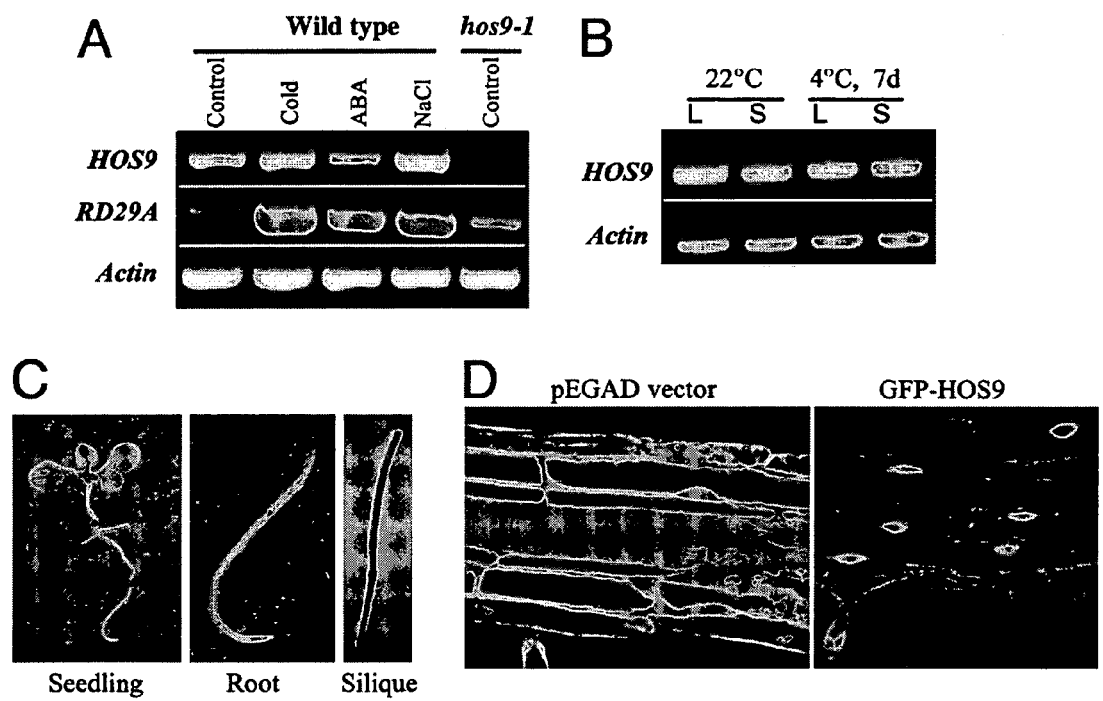
FIG. 6. shows the expression of the HOS9 gene and subcellular localization of HOS9 protein. (A) The HOS9 expression level was determined by RT-PCR. An actin gene was used as loading control. Control, no treatment; Cold, 0° C. for 48 h; ABA, 100 μM for 3 h; NaCl, 300 mM for 5 h. (B) Expression of HOS9 under different photoperiods at room temperature (22° C.) or low temperature (4° C., 7 d) by RT-PCR. Three micrograms of total RNA was used to synthesize the first-strand cDNA. An actin gene was used as loading control. L, long-day photoperiod; S, short-day photoperiod. (C) Histochemical staining of transgenic plants expressing HOS9 promoter::GUS.(D) The GFP-HOS9 fusion protein is localized in the nucleus. Confocal image of root cell in plants transformed with empty vector only (Left) and confocal image of root cell in GFP-HOS9 transgenic plants (Right).

The HOS9 gene encodes a putative homeodomain transcription factor of plant stress response that is localized to the nucleus (FIGS. 5–6). HOS9 is constitutively expressed and is not further induced by cold stress. Cold treatment increased the level of transcripts of the endogenous RD29A, and some other stress-responsive genes, to a higher level in hos9-1 than in wild-type plants. However, the C repeat/dehydration responsive element-binding factor (CBF) transcription factor genes that mediate a part of cold acclimation in plants including *Arabidopsis* did not have their response to cold altered by the hos9-1 mutation. Correspondingly, microarray analysis showed that none of the genes affected by the hos9-1 mutation are controlled by the CBF family. These results indicate that HOS9 is important for plant growth and development, and freezing tolerance, in part by affecting the activity of genes independent of the CBF pathway.

Expression of the endogenous CBF genes under cold stress are not affected by the hos9 mutation. The hos9 mutant plants are more sensitive to freezing stress. Identification of the HOS9 locus revealed that it encodes a homeodomain transcription factor. HOS9, a transcription factor, acts as a master switch of cold-responsive gene expression and cold tolerance in plants.

The hos9-1 mutation was identified in a screen for altered activity of the stress-controlled promoter of the RD29A gene. The hos9-1 mutant displays specific enhancement of cold induction of the RD29A::LUC reporter (FIGS. 1 and 3). Northern blot analysis confirmed the hyperinduction by cold but also revealed enhanced induction by ABA of both the luciferase and native RD29A transcripts. Discrepancies between the luminescence intensity and luciferase steady-state transcript level, as well as differences in expression between the RD29A promoter::LUC fusion gene and the native RD29A gene have been observed with other mutants and possible explanations have been discussed.

The effect of the hos9-1 mutation on constitutive freezing tolerance is quite clear, resulting in a decrease of maximum freezing tolerance by 3–6 degrees. This gene also appears to have a similar, perhaps somewhat less effect on the ability of the plants to cold acclimation (FIG. 2). This suggests that HOS9 mainly controls basal or constitutive freezing tolerance in *Arabidopsis*. In addition, it is possible that the role of HOS9 in cold acclimation is redundant with other regulatory factors.

The expression of the HOS9 gene is disrupted by the T-DNA insertion, and a HOS9 transcript was not detected (FIG. 6A). The HOS9 gene is constitutively expressed in wild-type plants and is not induced by cold or NaCl stress (FIG. 6A). This is in sharp contrast to the CBF gene family that is not expressed except after a short period after stress. HOS9 is the first *Arabidopsis* transcription factor to be identified that has been reported to control cold tolerance but not to affect the expression of CBF genes.

Because the CBF genes are induced normally by cold treatment in hos9-1 mutant plants, the cold sensitivity of hos9-1 must be largely the result of disruption of expression or function of genes other than those targeted by CBF, or the hos9-1 mutation has posttranscriptional effects on the function (activity) of CBF without disrupting accumulation of its transcript. Microarray analysis of hos9-1 mutant plants did not reveal the disruption of cold induction of any genes reported to be controlled by CBF (Table 1), indicating that HOS9 controls the expression of genes that are important for cold tolerance but are not part of the CBF regulon. However, because the microarray analyses of CBF target genes (Fowler & Thomashow (2002) Plant Cell 14, 1675–1690) included only 31.4% (8,000 of 25,500) of a full genome array, it is still possible that some genes targeted by CBF are among those whose expression is controlled also by HOS9 (The *Arabidopsis* Genome Initiative (2000) Nature 408, 796–815.). The HOS9 gene apparently does moderately affect the expression of some gene targets of CBF as seen from the enhancement of cold induction of RD29A, one of the targets of CBF. It appears that HOS9 is also be a negative regulator of some CBF target genes, as is true of HOS1. HOS9 must permit cold tolerance by mediating the constitutive activity of some genes or gene products that are essential for this trait. The loss of this activity in hos9-1 mutant plants results in increased expression of cold-induced genes by a compensating response to the increased cold sensitivity.

One of the earliest and most universal signal responses to cold exposure is the elevation of cytosolic Ca2+. The effect of hos9-1 mutation on cytosolic Ca2+ levels with F2 progeny of crosses between hos9-1 and aequorin expressing plants were examined. This technique showed that the relative cytosolic Ca2+ levels in hos9-1 and wild-type plants are identical. Thus, HOS9 gene functions occur after the stress-induced increase in cytosolic calcium.

"Cold stress" or "freezing" refers to any decrease in ambient or optimal temperature, including exposure to freezing temperatures, that cause a plant to attempt to acclimate itself to the decreased ambient temperature.

The terms "fragment", or "segment" or "portion" or "domain" refer to a nucleic acid or amino acid region derived from SEQ ID NO: 1 or SEQ ID NO: 2 of HOS9 such that expression or the fragment or segment or portion or domain of HOS9 confers or improves stress tolerance in plants. Such a fragment or segment or portion or a domain may have about 50 to about 100 contiguous nucleic acids or about 100 to about 500 contiguous nucleic acids; 20 to about 50 contiguous amino acids or about 50 to about 100 contiguous amino acids. One or more of such distinct segments or fragments or domains can also be fused or separated by an unrelated intervening sequence. The flanking sequences of such fragments or segments can be any nucleic acid or amino acid sequence.

A "substantially similar" nucleic acid or amino acid sequence refers to a nucleic acid sequence that is at least 70% identical to SEQ ID NO: 1 or SEQ ID NO: 2. A substantially similar sequence as used herein also relate to genetically engineered sequence with substitutions, insertions, deletions or modifications in the amino acid sequence. A substantially similar sequence as used herein also relates to differences in codon degenerecy and codon preference. The percent identity (% similarity) may relate to a short stretch of DNA or a peptide sequence or over the entire length of the peptide or the nucleic acid sequence. For example, a fragment of length 30 amino acids may exhibit 90% similarity for that 30 amino acid stretch as compared to a 65% similarity for the entire length of a protein of about 300 amino acids.

An "operably linked" sequence includes a functional connection between a promoter sequence and a second sequence of interest such as HOS9, wherein the promoter sequence initiates the transcription of the DNA sequence corresponding to the second sequence. The promoter sequence and the second sequence may be contiguous or separated by an intervening sequence. A first nucleic acid sequence is "operably linked" with a second nucleic acid sequence when the sequences are so arranged that the first nucleic acid sequence affects the function of the second nucleic-acid sequence. The two sequences may be part of a single contiguous nucleic acid molecule and may be adjacent. For example, a promoter is operably linked to a gene if the promoter regulates or mediates transcription of the gene in a cell. For example, HOS9 gene sequence is operably linked to a promoter, such as, a CaMV 35S promoter, capable of overexpressing HOS9.

By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host. For example, a gene whose sequence is identical to the host endogenous sequence, can be operably linked to a promoter sequence that is not the host gene's promoter.

"Nucleic acid or nucleic acid sequence" or "polynucleotide or polynucleotide sequence" refers to the sequence of a single- or double-stranded DNA or RNA molecule of genomic or synthetic origin, i.e., a polymer of deoxyribonucleotide or ribonucleotide bases, respectively. The nucleic acid can represent the sense or complementary (antisense) strand. Reference to HOS9 nucleic acid or a substantially similar sequence relate to DNA, RNA, genomic, cDNA, or a synthetic sequence.

"Native" refers to a naturally occurring ("wild-type") nucleic acid sequence.

An "isolated" nucleic acid sequence is substantially separated or purified away from other nucleic acid sequences with which the nucleic acid is normally associated in the cell of the organism in which the nucleic acid naturally occurs, i.e., other chromosomal or extrachromosomal DNA. The term includes nucleic acids that are biochemically purified so as to substantially remove contaminating nucleic acids and other cellular components. The term also includes recombinant nucleic acids and chemically synthesized nucleic acids. The term "substantially purified", as used herein, refers to a molecule separated from other molecules normally associated with it in its native state. For example, a substantially purified molecule is the predominant species present in a preparation, such as, isolated HOS9 nucleic acid.

A first sequence displays "substantial identity" or "substantial similarity" to a reference sequence if, when optimally aligned (with appropriate nucleotide insertions or deletions totaling less than 20 percent of the reference sequence over the window of comparison) with the other nucleic acid (or its complementary strand), there is at least about 70% nucleotide sequence identity, at least about 80% identity, at least about 85% identity, and at least about 90% identity over a comparison window of at least 20 nucleotide positions, at least 50 nucleotide positions, at least 100 nucleotide positions, and over the entire length of the first nucleic acid. Optimal alignment of sequences for aligning a comparison window may be conducted by the local homology algorithm of Smith and Waterman; by the homology alignment algorithm of Needleman and Wunsch; by the search for similarity method of Pearson and Lipman; by computerized implementations of these algorithms in the Wisconsin Genetics Software Package Release 7.0, (Genetics Computer Group, 575 Science Dr., Madison, Wis.), by nucleotide comparison using BLAST analysis at the National Center for Biotechnology Information (NCBI) resource center. The reference nucleic acid may be a full-length molecule or a portion or a fragment or a domain of a longer molecule. Alternatively, two nucleic acids are have substantial identity if one hybridizes to the other under stringent conditions, as routinely practiced in the art. Similar comparison can be performed at the amino acid level. Nucleic acid or amino acid sequence of HOS9 is compared against other sequences in databases to identify substantially similar or homologous sequences. A substantially similar sequence of HOS9 either at the nucleic acid level or at the amino acid level can be engineered using standard site directed mutagenesis kits to insert, delete, or modify amino acids. A substantially similar sequence of HOS9 can also have modified amino acids or other non-naturally occuring amino acids or amino acid analogs.

A "recombinant" nucleic acid is made by an artificial or in vitro combination of two otherwise separated segments of sequence, e.g., by chemical synthesis or by the manipulation of isolated segments of nucleic acids by genetic engineering techniques. Techniques for nucleic-acid manipulation are well-known (see for example Sambrook et al., Molecular Cloning: A Laboratory Manual, Cold Spring Harbor Press, 1989; Old, R. W. and Primrose, S. B. (1994). Principles of Gene Manipulation, 5th ed. Blackwell Science, Mailga et al., Methods in Plant Molecular Biology, Cold Spring Harbor Press, 1995).

"Amplification" of nucleic acids or "nucleic acid reproduction" refers to the production of additional copies of a nucleic acid sequence and is carried out, for example using polymerase chain reaction (PCR) technologies. In PCR, a primer or an oligo refers to a short oligonucleotide of defined sequence which is annealed to a DNA template to initiate the polymerase chain reaction.

"Transformed", "transfected", or "transgenic", or "genetically transformed" refers to a cell, seed, flower, tissue, organ, or organism into which has been introduced a foreign nucleic acid, such as a recombinant construct. Preferably, the introduced nucleic acid is integrated into the genomic DNA of the recipient cell, tissue, organ or organism such that the introduced nucleic acid is inherited by subsequent progeny. The nucleic acid may be stably integrated or transformed or transiently transformed. A "transgenic" or "transformed" cell or organism also includes progeny of the plant, cell or organism and progeny produced from a breeding program employing such a "transgenic" plant as a parent in a cross and exhibiting an altered phenotype and genotype resulting from the presence of a recombinant construct or construct. Seeds resulting from such a cross is also transgenic. A "transgenic plant" is a plant containing DNA sequences which were introduced by transformation or any other appropriate gene transfer mechanism. HOS9 transgenic plant refers to a genetically engineered plant that has at least one copy of the HOS9 gene (nucleic acid) or a fragment thereof either stably integrated or transiently expressed, where the nucleic acid is introduced exogenously.

"Obtaining" a transgenic plant generally refers to a genetically modified plant produced through any transformation technique. Progeny (T2, T3 and the like) of such a genetically modified plant obtained through self-crossing or back-crossing, or through any other breeding method are also included.

"Host cell" refers to any cell (e.g., mammalian cells, plant cells, insect cells, bacterial or viral cells), whether located in vitro or in vivo.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g. rRNA, tRNA); and other types of gene function as regulators of expression (regulator genes).

A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

"Expression" of a gene refers to the transcription of a gene to produce the corresponding mRNA and translation of this mRNA to produce the corresponding gene product, i.e., a peptide, polypeptide, or protein. Gene expression is controlled, regulated or modulated by regulatory elements including 5' regulatory elements such as promoters and appropriate transcription factors. For example, expression of HOS9 or a fragment thereof results in HOS9 mRNA and a protein or polypeptide that corresponds to the HOS9 nucleic acid.

The terms "recombinant DNA", "recombinant DNA construct", "recombinant construct", "expression construct" or "expression cassette" refer to any agent such as a plasmid, phagemid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner using well-known recombinant DNA techniques.

"Complementary" refers to the association of nucleic acid sequences by base-pairing (G-C-T pairs with the complementary sequence C-G-A). Complementarity between two single-stranded nucleic acids may be partial, if only some of the nucleic acids pair are complementary; or complete, if all bases pair are complementary.

"Homology" refers to common evolutionary descent. Homologs have common origins but may or may not have common activity. Genes that share an arbitrary threshold level of similarity determined by alignment of matching bases are termed homologous. They are inherited from a common ancestor which possessed the structure. Homology also refers to the concept of similar functional properties among different nucleic acids or proteins. HOS9 may have functional homologs in other species that may also share structural similarity at the amino acid level.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in many tissues of a plant throughout plant development. Tissue-, organ- or cell-specific promoters are expressed only or predominantly in a particular tissue, organ, or cell type, respectively. A promoter may display "enhanced" expression, i.e., a higher level of expression, in one part (e.g., cell type, tissue, or organ) of the plant compared to other parts of the plant. Temporally regulated promoters function only or predominantly during certain periods of plant development or at certain times of day. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by cold, light, heat, stress, flooding or drought, phytohormones, wounding, or chemicals such as ethanol, jasmonate, or salicylic acid.

"Vector" or "expression vector" refers to any genetic element, such as a plasmid, phage, transposon, cosmid, chromosome, virus, virion, and the like, capable of replication or being expressed when associated with the proper control elements. Thus, the term includes cloning and expression vehicles, as well as viral vectors. "Expression vector" also refers to a recombinant DNA molecule that includes a desired coding sequence and relevant nucleic acid sequences such as a promoter sequence necessary for the expression of the operably linked coding sequence in a particular host organism such as plants. Eukaryotic cells are generally known to utilize promoters, enhancers, and termination and polyadenylation signals. Expression vectors that include a nucleic acid sequence encoding HOS9 peptide or a fragment there are capable of transforming plants or plant cells to confer cold tolerance. "Expression construct" or "expression cassette" refer to a segment within a vector that includes a promoter sequence and a coding sequence.

The term "condition" or "conditioning" refers to providing increased cold tolerance or increased ability to respond to cold stress. This conditioning may be due to an increase in gene expression or an activated state due to post-translational modifications. For example, an increase in the HOS9 gene product due to overexpression of HOS9 gene renders the plant to better adapt to cold stress by modulating the activity of downstream genes or gene products.

Any promoter capable of initiating transcription in plants can be used as a 5' regulatory sequence for modulating expression of HOS9 or a fragment thereof in plants. Some of the examples include a plant RNA polymerase II promoter and a CaMV 35S viral promoter. Promoter elements such as the TATA box or Goldberg-Hogness box are generally required for correct expression of eukaryotic genes in vitro and initiation of transcription in vivo. Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart). In addition, promoters generally include additional upstream activating sequences or enhancers extending from around −100 bp to −1,000 bp or more upstream of the transcription initiation site.

When fused to heterologous DNA sequences such as a HOS9 coding sequence or a fragment of HOS9 capable of imparting cold or freezing tolerance in plants, such promoters typically cause the fused sequence to be transcribed. Promoter fragments that include regulatory sequences can be added (for example, fused to the 5' end of, or inserted within, an active promoter having its own partial or complete regulatory sequences. Alternatively, heterologous regulatory sequences can be added to the 5' upstream region of an inactive, truncated promoter, e.g., a promoter including only the core TATA and, sometimes, the CCAAT elements.

Promoters are typically comprised of multiple distinct "cis-acting transcriptional regulatory elements," or simply "cis-elements," each of which confers a different aspect of the overall control of gene expression. "Cis elements" bind trans-acting protein factors that regulate transcription. Some cis elements bind more than one factor, and trans-acting transcription factors may interact with different affinities with more than one cis element.

Plant promoters can also include promoters produced through the manipulation of known promoters to produce synthetic, chimeric, or hybrid promoters. Such promoters can also combine cis elements from one or more promoters, for example, by adding a heterologous regulatory sequence to an active promoter with its own partial or complete regulatory sequences. Chimeric or hybrid promoters may include at least one known cis element such as elements that are regulated by numerous environmental factors such as cold, drought, light, heat, or stress; elements that are regulated or induced by pathogens or chemicals, and the like. Such elements may either positively or negatively regulate gene expression, depending on the conditions. Examples of cis elements include, but are not limited to cold-responsive elements.

For a number of agronomic traits such providing cold tolerance, transcription of a gene or genes of interest, such as HOS9, is desirable in multiple tissues to confer the desired characteristic(s). The availability of suitable promoters that regulate transcription of operably linked genes in selected target tissues of interest is desirable if selective expression is preferred. For example, selective expression of cold-tolerance genes in fruits such as citrus fruits is desirable. The promoter sequences capable of being expressed in in multiple tissues and stages of plant development are also preferred.

Any plant can be selected for the identification of genes and regulatory sequences. Examples of suitable plant targets for the isolation of genes and regulatory sequences would include but are not limited to alfalfa, apple, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nut, oat, oil palm, oil seed rape, okra, olive, onion, orange, an ornamental plant, palm, papaya, parsley, parsnip, pea, peanut, pear, pepper, persimmon, pine, pineapple, plantain, pomegranate, poplar, potato, pumpkin, quince, radiata pine, radiscchio, radish, rapeseed, raspberry, rice, rye, sorghum, Southern pine, soybean, spinach, squash, stone fruits (e.g., peach, plum, nectarine, apricot, and cherry), strawberry, sugarbeet, sugarcane, sunflower, sweet potato, sweetgum, tangerine, tea, tobacco, tomato, triticale, turf, turnip, a vine, watermelon, wheat, yams, and zucchini.

Any number of methods can be used to isolate fragments of HOS9. A PCR-based approach can be used to amplify flanking regions from a genomic library of a plant using publicly available sequence information. A number of methods are known to those of skill in the art to amplify unknown DNA sequences adjacent to a core region of known sequence. Methods include but are not limited to thermal asymmetric inter-laced PCR (TAIL-PCR), inverse PCR (IPCR), vectorette PCR, Y-shaped PCR and genome walking approaches. HOS9 cDNA is isolated from a cDNA library. By using probes designed from the disclosed HOS9 sequence, cDNAs from other species can be isolated using standard techniques. Degenerate probes of HOS9 can also be designed and used.

Nucleic acid fragments can also be obtained by other techniques such as by directly synthesizing the fragment by chemical means, as is commonly practiced by using an automated oligonucleotide synthesizer. Fragments can also be obtained by application of nucleic acid reproduction technology, such as the PCR (polymerase chain reaction) technology by recombinant DNA techniques generally known to those of skill in the art of molecular biology. Regarding the amplification of a target nucleic-acid sequence (e.g., by PCR) using a particular amplification primer pair, "stringent PCR conditions" refer to conditions that permit the primer pair to hybridize only to the target nucleic-acid sequence to which a primer having the corresponding wild-type sequence (or its complement) would bind and preferably to produce a unique amplification product.

Plant expression constructs may also include more than one expressible gene sequence, each operably linked to a different promoter. For example, a first coding sequence HOS9 can be operably linked to a first promoter and a second coding sequence CBF can be functionally linked to a different or same promoter within the same construct or a different construct. A number of promoters have utility for plant gene expression for any gene of interest including but not limited to selectable markers, scorable markers, genes for pest tolerance, disease tolerance, nutritional enhancements and any other gene of agronomic interest. Examples of constitutive promoters useful for plant gene expression include but are not limited to, the cauliflower mosaic virus (CaMV) P-35S promoter, which confers constitutive, high-level expression in most plant tissues including monocots; a tandemly duplicated version of the CaMV 35S promoter, the enhanced 35S promoter (P-e35S) the nopaline synthase promoter, the octopine synthase promoter; and the figwort mosaic virus (P-FMV) promoter and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), or (5) chemicals such as methyl jasmonate, salicylic acid or (6) organ-specific promoters (e.g., Roshal et al., EMBO J. 6:1155, 1987; Schernthaner et al., EMBO J. 7:1249, 1988; Bustos et al., Plant Cell 1:839, 1989). The promoters are capable of transcribing operably linked DNA sequences and can be operably linked to any gene of interest in an expression construct.

Suitable promoters also include plant stress inducible promoter, viral coat protein promoter, a tissue-specific promoter, a monocot promoter, a ubiquitin promoter, a CaMV 35S promoter, a CaMV 19S promoter, a nos promoter, an Adh promoter, a sucrose synthase promoter, a tubulin promoter, a napin promoter, an actin promoter, a cab promoter, a PEPCase promoter, a 7S-alpha'-conglycinin promoter, an R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a PM, promoter, a root-cell promoter, an ABA-inducible promoter or a turgor-inducible promoter, and any other stress inducible promoters. Stress inducible promoter are particularly helpful. Exemplary transiently activated stress-inducible plant promoters are described in U.S. Pat. No. 6,414,221. "Super" promoters that include multiple activator sequences (e.g., a triple repeat of the ocs activator sequence along with mas activator elements fused to the mas promoter) can also be used to achieve high expression of introduced genes (Ni et al., (1995) Plant J. 7, 661–676; U.S. Pat. No. 5,955,646).

PLACE is a database of nucleotide sequence motifs found in plant cis-acting regulatory DNA elements. Depending upon the need for using a specific cis-acting element, the regulatory database can be searched. Documents for each motif in the PLACE database contains a motif sequence, a brief definition and description of each motif, and relevant literature with PubMed ID numbers and GenBank accession numbers. (Higo et al., 1999 Plant cis-acting regulatory DNA elements (PLACE) database: Nucl. Acids Res. 27: 297–300).

PlantCARE is also a database of plant promoters and their cis-acting regulatory elements. PlantCARE is a database of plant cis-acting regulatory elements, enhancers and repressors. Regulatory elements are represented by positional matrices, consensus sequences and individual sites on particular promoter sequences. (Lescot et al., 2002 PlantCARE, a database of plant cis-acting regulatory elements and a portal to tools for in silico analysis of promoter sequences. Nucl. Acids Res. 2002 30: 325–327).

PlantProm a plant promoter database, is an annotated, non-redundant collection of proximal promoter sequences for RNA polymerase II with experimentally determined transcription start site(s), TSS, from various plant species. It provides DNA sequence of the promoter regions with TSS, taxonomic/promoter type classification of promoters and Nucleotide Frequency Matrices (NFM) for promoter elements: TATA-box, CCAAT-box and TSS-motif (Inr). (Shahmuradov et al., 2003 PlantProm: a database of plant promoter sequences. Nucl. Acids Res. 31: 114–117).

Plant expression constructs can include RNA processing signals, e.g., introns, which may be positioned upstream or downstream of a polypeptide-encoding sequence in the transgene. In addition, the expression constructs may include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions. 5' non-translated regions of a mRNA can play an important role in translation initiation and can also be a genetic component in a plant expression construct. For example, non-translated 5' leader sequences derived from heat shock protein genes have been demonstrated to enhance gene expression in plants. These additional upstream and downstream regulatory sequences may be derived from a source that is native or heterologous with respect to the other elements present on the expression construct. Those of skill in the art are aware of the constructs.

Methods of testing gene expression in transient assays are known to those of skill in the art. Transient expression of marker genes has been reported using a variety of plants, tissues and DNA delivery systems. For example, types of transient analyses can include but are not limited to direct gene delivery via electroporation or particle bombardment of tissues in any transient plant assay using any plant species of interest. Such transient systems would include but are not limited to protoplasts from suspension cultures in wheat (Zhou et al., Plant Cell Reports 12:612. 1993), electroporation of leaf protoplasts of wheat (Sethi et al., J. Crop Sci. 52:152, 1983); electroporation of protoplast prepared from corn tissue (Sheen, J. The Plant Cell 3:225, 1991), or particle bombardment of specific tissues of interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker can be used in a transient assay. Preferred marker genes for transient analyses of the promoters or 5' regulatory sequences include a beta.-glucuronidase (GUS) gene or a green fluorescent protein (GFP) gene. The expression constructs containing the 5' regulatory sequences operably linked to a marker gene are delivered to the tissues and the tissues are analyzed by the appropriate mechanism, depending on the marker.

Suitable expression constructs for introducing exogenous DNA into plant cells would include but are not limited to disarmed Ti-plasmids for *Agrobacterium*-mediated methods. These constructs can contain a resistance marker, 1-2 T-DNA borders, and origins of replication for *E. coli* and *Agrobacterium* along with one or more genes of interest and associated regulatory regions. Those of skill in the art are aware that for *Agrobacterium*-mediated approaches a number of strains and methods are available. Such strains would include but are not limited to *Agrobacterium* strains GV3101, C58, LBA4404, EHA101 and EHA105.

Exemplary nucleic acids which may be introduced by the methods encompassed disclosed herein include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or not present in the form, structure, and the like, as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

The plant transformation constructs containing the nucleic acid sequences disclosed herein may be introduced into plants by any plant transformation method. Several methods are available for introducing DNA sequences into plant cells and are well known in the art. Suitable methods include but are not limited to bacterial infection (e.g., with *Agrobacterium* as described above), binary bacterial artificial chromosome constructs, direct delivery of DNA (e.g. via PEG-mediated transformation, desiccation/inhibition-mediated DNA uptake, electroporation, agitation with silicon carbide fibers), and acceleration of DNA coated particles (reviewed in Potrykus, Ann. Rev. Plant Physiol. Plant Mol. Biol., 42:205, 1991; Gelvin, S. B. 1998. The introduction and expression of transgenes in plants. Curr. Opin. Biotechnol. Curr. Opin. Biotechnol. 9:227–232).

EXAMPLES

The following examples are to be considered as exemplary and not restrictive in character.

Example 1

Isolation, Identification and Analysis of Hos9-1 Mutant

Isolation of the hos9-1 Mutant. A genetic loci that affected cold perception and signaling leading to target gene induction was identified using an *A. tumefaciens*-mediated T-DNA insertion/activation mutagenesis (pSKI015 vector) of *Arabidopsis* plants that were expressing a homozygous firefly luciferase reporter gene driven by the stress-responsive RD29A promoter. The T2 plants were used to screen for mutants that exhibited altered expression of RD29A::LUC in response to low temperature, ABA, or osmotic treatment. A mutant, hos9-1, was isolated, which displays hyperexpression of the RD29A::LUC marker specifically in response to low-temperature treatment (FIGS. 1A and B) and not to ABA or NaCl treatment (FIG. 1 C–F) compared to wild-type seedlings. Quantification of RD29A::LUC expression indicated that cold-activated RD29A::LUC expression in hos9-1 mutant seedlings was >3-fold higher than that in wild type (FIG. 1G) and remained substantially higher in hos9-1 plants for 3 h or longer (FIG. 1H).

hos9-1 mutant plants were backcrossed with wild type, and all of the resulting $F_1$ plants exhibited a wild-type phenotype and were resistant to bialaphos (conferred by the basta gene on the pSKI015 vector) when transferred to soil. The $F_2$ progeny of the selfed $F_1$ plants segregated in an 3:1 ratio of wild type: mutant phenotype indicating that hos9-1 is a recessive mutation in a single nuclear gene. Analysis of the bialaphos resistance and the presence of the basta gene by PCR of the F1 and F2 plants also revealed the presence of a single functional T-DNA that is inserted in the genome of the hos9-1 mutant.

hos9-1 plants are hypersensitive to freezing treatment. The effect of the hos9-1 mutation on plant freezing tolerance was evaluated by performing a whole-plant-freezing test (FIG. 2A). Without cold acclimation neither wild-type nor hos9-1 plants can tolerate freezing treatment at −4° C. or lower. When grown and then acclimated at 4° C. for 1 week under a long-day photoperiod, the majority of the wild-type plants survived freezing treatment as low as −8° C., but none of the hos9-1 mutant plants survived freezing treatments at −4° C. or lower temperatures (FIG. 2A). Similar results were obtained after growing and acclimating the plants under a short-day photoperiod. An electrolyte leakage assay was also performed to quantify the freezing tolerance of hos9-1 (FIG. 2B). Without cold acclimation, hos9-1 plants have considerably reduced tolerance to freezing treatments compared to wild-type plants. In addition, after a 4° C. treatment for 1 week hos9-1 plants were unable to fully acclimate, compared to wild-type plants (FIG. 2B). These results indicate that the hos9-1 mutation both decreases constitutive cold tolerance and impairs cold acclimation ability.

Example 2

Cloning of HOS9, Complementation of Hos9-1 Mutant and Structural Analysis of HOS9

Identification of the HOS9 Locus was determined by cloning genomic fragments. The genomic fragment flanking the left border of the T-DNA insert of hos9-1 mutant plants was isolated by thermal asymmetric interlaced PCR. Database searches revealed that the T-DNA tag was inserted at nucleotide 51,349 in BAC F2I9 on *Arabidopsis* chromosome 2, a position 319 bp upstream of the predicted TGA stop codon of gene At2g01500 (FIG. 5A). Two pairs of primers were designed to determine whether this T-DNA insertion cosegregates with the hos9-1 mutant phenotype. The T-DNA insert was homozygous in all plants (48 of 48) that were homozygous for the hos9-1 mutant phenotype.

Using a genomic fragment containing the putative HOS9 gene, hos9-1 mutant plants were complemented. When the wild-type copy of the HOS9 locus was introduced into hos9-1 plants, RD29A::LUC expression returned to the wild-type level (FIG. 5B). The freezing tolerance (FIG. 5C), flowering time and trichome formation phenotypes (data not shown) of hos9-1 plants also reverted to nearly wild type in the complemented mutant plants.

HOS9 encodes a putative homeobox protein. There is a full-length cDNA clone (Ceres_18820) available for the HOS9 gene, and the sequence information by RT-PCR analysis. HOS9 is composed of four exons and three introns (FIG. 5A) and it encodes a 271-aa polypeptide with a predicted molecular mass of 31,435 Da. Comparison of the predicted HOS9 amino acid sequence with those of other gene products revealed that HOS9 shares greatest similarity, within the homeodomain motif, with the *Arabidopsis* proteins WUSCHEL (WUS), and PRESSED FLOWER (PRS) (FIG. 5D). The homeodomain encoded by a 180-bp consensus DNA sequence, called a homeobox, is present in a number of proteins involved in developmental processes. Homeobox-containing proteins act as transcription factors, regulating the expression of target genes via sequence-specific recognition.

Example 3

Regulation of Gene Expression in Hos9-1 Plants

Expression of the endogenous RD29A gene was monitored in hos9-1 mutant plants by northern hybridization using total RNA extracted from hos9-1 and wild-type seedlings, which were exposed or not exposed to low temperature, ABA, or NaCl (FIG. 3). Cold induction of the luciferase transcript and the endogenous RD29A gene was higher in the hos9-1 mutant than in the wild-type plants at 24- and 48-h time points (FIG. 3A). However, no significantly higher induction of luciferase and the endogenous RD29A transcripts than in wild type was observed in hos9-1 plants in response to NaCl treatment (FIG. 3A). Unlike the luciferase image, the transcript levels of luciferase and RD29A appear higher in hos9-1 in response to ABA treatments (FIG. 3A). The expression levels of the cold-specific transcription factors that activate the expression of cold-regulated genes and mediate cold acclimation were not altered in hos9-1 mutant plants compared to wild-type plants (FIG. 3B).

Example 4

Effects of Hos9-1 Mutation on Plant Growth and Development

Plants that carry the hos9-1 mutation grow more slowly than wild-type plants under greenhouse conditions (FIG. 4). The final size of hos9-1 plants after flowering is smaller (FIGS. 4C and F) and leaves of hos9-1 are narrower and smaller (FIGS. 4 C and D). Both shoots and roots of hos9-1 plants exhibited slower growth rates when measured as either fresh (FIG. 4A) or dry (FIG. 4B) weight gains. There are fewer trichomes formed on the hos9-1 leaves at different developmental stages (FIGS. 4D and E). Under the experimental conditions used, hos9-1 plants also flower >10 d later than wild-type plants (FIG. 4F and data not shown). Because in *Arabidopsis*, flowering time can be influenced by exposing plants to low nonfreezing temperatures (i.e., vernalization), the vernalization responses of hos9-1 and wild-type plants was tested. Even though hos9-1 plants cannot be induced to flower as early as wild-type plants by cold treatment for as long as 50 d, they do respond to vernalization treatment (FIG. 4G) and display normal basal transcript level of flowering time locus C (FLC) gene (FIG. 3A), the major mediator of vernalization.

Example 5

HOS9 Gene Expression and HOS9 Subcellular Localization

HOS9 is constitutively expressed, and perhaps its expression is decreased somewhat after ABA treatment of seedlings (FIG. 6A). Its expression is also not regulated by different day lengths (FIG. 6B). To determine the tissue and cell type expression pattern of HOS9, the HOS9 promoter was fused to the GUS reporter gene, and GUS activities were examined in transgenic *Arabidopsis* plants. GUS expression was observed in all tissues of young seedlings but was relatively stronger in the vascular tissues and weaker in root tips (FIG. 6C). To examine the subcellular localization of the HOS9 protein, HOS9 was fused in-frame to the C terminus of the GFP and expressed under the control of the CaMV 35S promoter. Confocal imaging of GFP fluorescence in the transgenic plants revealed that the GFP-HOS9 fusion protein is present in the nucleus (FIG. 6D).

Example 6

Microarray Analysis of hos9-1 Mutant and Gene Regulation

Global gene expression in the hos9-1 mutant under cold treatment was performed by using the Affymetrix near-full genome GeneChip array. Analyses of the microarray data indicated that, compared to wild-type plants, the expression of 140 genes was higher in the hos9-1 mutant by at least 3-fold (Table 1) and that of 35 genes was lower by at least 2-fold in the hos9-1 mutant (Table 2). The steady-state RNA levels of three of the genes was examined by RT-PCR to confirm the microarray results. The expression of the At2g46400 and At2g32210 genes was higher in the hos9-1 mutant and that of At5g44420 was lower in the mutant, consistent with results obtained from the microarrays (FIG. 3C).

Of the 140 genes that were more expressed in the hos9-1 mutant, 41 appeared as cold-induced in a microarray analysis of cold induction using the Affymetrix array (Table 3). In Tables 1–3, Affymetrix changes in gene expression were analyzed by comparing values for a wild-type sample to those for a hos9-1 sample. Up- or down-regulation is expressed by either + or − in "hos9-1_vs_C24_0C-24H_Signal Log Ratio" valus, respectively. Signal log ratio is an index, determined by the Affymetrix MICROARRAY SUITE program, to estimate the magnitude and direction of change of a gene transcript in pair comparison. If the signal log ratio is equal to or greater than 0, fold change is obtained with 2 (Signal Log Ratio); otherwise, (−1)×2−(Signal Log Ratio) is used. In the Detection column, calls include "P" for "Present," "A" for "Absent," and "M" for "Marginal." The HOS9 gene is apparently important for both constitutive expression and cold-induced expression of genes that may be required for full tolerance to freezing stress.

Example 7

Overexpression of HOS9

HOS9 gene driven by a super promoter improved cold tolerance in plants. Four week old plants were kept for an additional 8 days at room temperature (25° C.) or 4° C. (cold acclimattion) and then exposed to indicated temperatures for 7 days (Table 4). At the end of seven days, percent (%) surviving plants were determined. Numbers indicate the % surviving plants without acclimation and in parentheses with acclimation. C24 is the parent line of the hos9 mutant. hos9 indicates the mutant line. HOS9 SUPER P-1, 2 are lines of C24 transformed with the HOS9 gene driven by a SUPER promoter. The HOS9 overexpressing lines exhibit at least 5 times the normal level of HOS9 transcript. The results indicate that HOS9 overexpressing lines (non-acclimated and acclimated) show increased or improved cold tolerance to temperatures ranging from +4° C. to −10° C. for a period of about 7 days (Table 4). Expression of HOS9 leads to improved stress tolerance to freezing temperatures.

TABLE 4

Overexpression of HOS9

| Treatment (° C.) | C24 | HOS9 | HOS9 SUPER P-1 | HOS9 SUPER P-1 |
|---|---|---|---|---|
| | | % Surviving Plants | | |
| 4 | 100 (100) | 100 (100) | 100 (100) | 100 (100) |
| −2 | 95 (100) | 0 (0) | 100 (100) | 100 (100) |
| −4 | 40 (85) | 0 (0) | 100 (100) | 100 (100) |
| −6 | 0 (50) | 0 (0) | 100 (100) | 100 (100) |
| −8 | 0 (20) | 0 (0) | 100 (100) | 100 (100) |
| −10 | 0 (0) | 0 (0) | 100 (100) | 100 (100) |

TABLE 1

Changes of gene expression in hos9-1, genes with higher expression in hos9-1 by 3-fold

| AGI ID | Gene Title | hos9-1_vs_ C24_0C-24H_ Signal Log Ratio | C24-0C-24H_ Signal | C24-0C-24H_ Detection | hos9-1_0C-24H_ Signal | hos9-1_0C-24H_ Detection |
|---|---|---|---|---|---|---|
| At3g09870 | auxin-induced (indole-3-acetic acid induced) protein family | 5.6 | 2.7 | A | 130.2 | P |
| At2g37430 | C2H2-type zinc finger protein-related | 4.7 | 11.1 | A | 280.4 | P |
| At3g13370 | hypothetical protein | 4.7 | 1.1 | A | 35.5 | P |
| At3g21080 | expressed protein | 4.7 | 8.8 | A | 342.4 | P |
| At3g12910 | expressed protein | 4.1 | 9.2 | A | 148.6 | P |
| | AFFX-Athal-25SrRNA_s_at | 3.9 | 145.3 | P | 4123 | P |
| At2g32030 | GCN5-related N-acetyltransferase (GNAT) family | 3.7 | 104 | P | 1401 | P |
| At5g51190 | AP2 domain transcription factor, putative | 3.5 | 89.7 | P | 899.4 | P |
| At1g05575 | expressed protein | 3.3 | 142.7 | A | 934.1 | P |
| At5g46295 | expressed protein | 3.3 | 35.5 | A | 197.2 | P |
| At1g35210 | expressed protein | 3.3 | 76 | P | 1333 | P |
| At1g30040 | gibberellin 2-oxidase (GA2-oxidase) (ga2ox2) | 3.2 | 86.9 | A | 929.3 | P |
| At3g28620 | zinc finger (RING finger) protein family | 3.2 | 22.7 | A | 161.9 | P |
| At3g55840 | nematode resistance protein-related protein | 3.1 | 242.3 | P | 2236 | P |
| At5g52760 | heavy-metal-associated domain-containing protein | 3 | 313.7 | P | 2518 | P |
| At5g57220 | cytochrome P450, putative | 2.9 | 150.7 | P | 1488 | P |
| At4g30430 | senescence-associated protein family | 2.8 | 102.5 | A | 721.5 | P |
| At4g37290 | expressed protein | 2.8 | 30.8 | A | 262 | P |
| At1g27820 | hypothetical protein | 2.8 | 32.3 | A | 337.6 | P |
| At1g15010 | expressed protein | 2.7 | 242.4 | P | 1692 | P |
| At4g24570 | mitochondrial carrier protein family | 2.7 | 631.6 | P | 4458 | P |
| At3g55980 | expressed protein | 2.7 | 569.8 | P | 3894 | P |
| At5g54490 | calcium-binding protein, putative | 2.7 | 585 | P | 4120 | P |
| At5g64870 | nodulin-related | 2.7 | 161.1 | P | 993.2 | P |
| At2g46400 | WRKY family transcription factor | 2.6 | 892.4 | P | 4361 | P |

TABLE 1-continued

Changes of gene expression in hos9-1, genes with higher expression in hos9-1 by 3-fold

| AGI ID | Gene Title | hos9-1_vs_ C24_0C-24H_ Signal Log Ratio | C24-0C-24H_ Signal | C24-0C-24H_ Detection | hos9-1_0C-24H_ Signal | hos9-1_0C-24H_ Detection |
|---|---|---|---|---|---|---|
| At3g23250 | myb family transcription factor(MYB15) | 2.6 | 35.8 | A | 236.1 | P |
| At5g22380 | No apical meristem (NAM) protein family | 2.6 | 214 | P | 1254 | P |
| At4g17490 | ethylene responsive element binding factor (ERF6) | 2.6 | 65.2 | A | 461.7 | P |
| At1g28370 | ethylene responsive element binding factor 11, EREBP11/ERF11) | 2.5 | 365.6 | P | 2024 | P |
| At3g01830 | calmodulin-related protein, putative | 2.5 | 129 | P | 795.5 | P |
| At3g28600 | AAA-type ATPase family | 2.5 | 26.5 | A | 156.7 | P |
| At1g61340 | F-box protein family | 2.4 | 363.3 | A | 2327 | P |
| At3g43250 | hypothetical protein | 2.4 | 43 | M | 270.6 | P |
| At5g26920 | calmodulin-binding protein | 2.4 | 1241.8 | P | 6901 | P |
| At1g57990 | purine permease-related | 2.4 | 579.3 | P | 3367 | P |
| At2g35710 | glycogenin glucosyltransferase (glycogenin) - related | 2.3 | 162 | P | 1080 | P |
| At2g20145 | disease resistance protein (TIR class), putative | 2.3 | 471.8 | P | 2334 | P |
| At1g56060 | hypothetical protein | 2.3 | 749.5 | P | 3804 | P |
| At1g76210 | expressed protein | 2.3 | 28.3 | A | 154.5 | P |
| At3g10930 | expressed protein | 2.3 | 130.8 | P | 611 | P |
| At4g23210 | serine/threonine kinase - like protein | 2.3 | 175.1 | P | 952 | P |
| At3g50930 | AAA-type ATPase family | 2.3 | 1016.2 | P | 5180 | P |
| At5g42380 | calmodulin-related protein, putative | 2.3 | 468.2 | P | 1878 | P |
| At5g45630 | hypothetical protein | 2.3 | 108.5 | P | 490.8 | P |
| At1g44130 | nucellin protein, putative | 2.3 | 27.7 | A | 151.4 | P |
| At2g35715 | expressed protein | 2.2 | 70.9 | A | 320.5 | P |
| At2g17040 | No apical meristem (NAM) protein family | 2.2 | 20.5 | A | 229.9 | P |
| At3g22910 | calcium-transporting ATPase (calcium pump), putative | 2.2 | 1152.9 | P | 5720 | P |
| At1g24140 | metallo proteinase - related | 2.1 | 173.5 | P | 748.4 | P |
| At1g78410 | expressed protein | 2.1 | 157.3 | P | 613.6 | P |
| At1g19380 | expressed protein | 2.1 | 238.5 | P | 1192 | P |
| At1g68840 | AP2 domain protein RAP2.8 (RAV2) | 2.1 | 621.9 | P | 2877 | P |
| At1g13340 | expressed protein | 2.1 | 684.6 | P | 2338 | P |
| At3g17690 | cyclic nucleotide-binding transporter 2 (CNBT2/CNGC19) | 2.1 | 28.2 | A | 119.3 | P |
| At1g66090 | disease resistance protein (TIR-NBS class), putative | 2.1 | 680.5 | P | 3025 | P |
| At4g12190 | C3HC4-type zinc finger protein family | 2.1 | 90.1 | P | 302.1 | P |
| At4g29780 | expressed protein | 2.1 | 518.2 | P | 2530 | P |
| At4g39670 | expressed protein | 2.1 | 900.3 | P | 4212 | P |
| At3g57450 | expressed protein | 2.1 | 524.2 | P | 2622 | P |
| At1g10340 | ankyrin repeat protein family | 2 | 632.1 | P | 2223 | P |
| At1g21110 | O-methyltransferase 1, putative | 2 | 111.4 | P | 461.7 | P |
| At1g19770 | purine permease-related | 2 | 1271.8 | P | 5122 | P |
| At3g16720 | RING zinc finger protein - related | 2 | 256.9 | P | 1014 | P |
| At3g28580 | AAA-type ATPase family | 2 | 78 | P | 279.5 | P |
| At1g18570 | myb family transcription factor | 2 | 125.4 | A | 415.9 | P |
| At4g38560 | Phospholipase like protein | 2 | 38.2 | A | 173.6 | P |
| At3g57950 | hypothetical protein | 2 | 29.4 | A | 122.7 | P |
| At5g01380 | transcription factor GT-3a | 2 | 55.3 | A | 222.2 | P |
| At5g39670 | calcium-binding EF-hand family protein | 2 | 889.9 | P | 3473 | P |
| At5g52750 | heavy-metal-associated domain-containing protein | 2 | 668.2 | P | 2412 | P |
| At4g14365 | expressed protein | 2 | 1192 | P | 6091 | P |
| At2g38470 | WRKY family transcription factor | 1.9 | 1705.4 | P | 6282 | P |
| At2g30020 | protein phosphatase 2C (PP2C), putative | 1.9 | 165.5 | P | 587.6 | P |
| At2g02140 | plant defensin protein, putative (PDF2.6) | 1.9 | 7.7 | A | 43.9 | P |
| At2g02010 | glutamate decarboxylase | 1.9 | 254.7 | P | 1103 | P |
| At1g76650 | calcium-binding EF-hand family protein | 1.9 | 154.3 | P | 562.4 | P |
| At3g02840 | expressed protein | 1.9 | 164 | P | 788.6 | P |
| At1g30370 | lipase (class 3) family | 1.9 | 122.4 | A | 402.2 | P |
| At4g27280 | calcium-binding EF-hand family protein | 1.9 | 3174.7 | P | 11729 | P |
| At3g44260 | CCR4-associated factor 1-related protein | 1.9 | 138.9 | P | 510.5 | P |
| At3g48640 | hypothetical protein | 1.9 | 906.7 | P | 3437 | P |
| At3g50770 | calmodulin-related protein, putative | 1.9 | 240.3 | P | 797.4 | P |
| At3g59080 | expressed protein | 1.9 | 177.8 | P | 814 | P |
| At3g61190 | BON1-associated protein 1 (BAP1) | 1.9 | 1221.4 | P | 5343 | P |
| At5g01540 | receptor lectin kinase, putative | 1.9 | 386 | P | 1232 | P |
| At5g60800 | heavy-metal-associated domain-containing protein | 1.9 | 119.4 | A | 516.2 | P |
| At3g56880 | expressed protein | 1.9 | 2060.1 | P | 7607 | P |
| At1g58420 | expressed protein | 1.9 | 210.7 | P | 850.3 | P |
| At2g45760 | C2 domain-containing protein | 1.9 | 145.9 | P | 515.1 | P |
| At2g32140 | disease resistance protein (TIR class), putative | 1.8 | 73.8 | P | 395.4 | P |
| At2g32190 | expressed protein | 1.8 | 1051.7 | P | 3318 | P |
| At1g72920 | disease resistance protein (TIR-NBS class), putative | 1.8 | 125.4 | P | 451.6 | P |
| At1g74710 | isochorismate synthase 1 (isochorismate mutase) (ICS1) | 1.8 | 541.9 | P | 1773 | P |
| At1g72520 | lipoxygenase (LOX), putative | 1.8 | 301.6 | P | 1056 | P |
| At1g63750 | disease resistance protein (TIR-NBS-LRR class), putative | 1.8 | 107.2 | P | 419.2 | P |
| At1g73800 | calmodulin-binding protein | 1.8 | 899.8 | P | 3406 | P |
| At1g01560 | mitogen-activated protein kinase (MAPK), putative (MPK11) | 1.8 | 1402 | P | 4621 | P |

TABLE 1-continued

Changes of gene expression in hos9-1, genes with higher expression in hos9-1 by 3-fold

| AGI ID | Gene Title | hos9-1_vs_ C24_0C-24H_ Signal Log Ratio | C24-0C-24H_ Signal | C24-0C-24H_ Detection | hos9-1_0C-24H_ Signal | hos9-1_0C-24H_ Detection |
|---|---|---|---|---|---|---|
| At4g33050 | expressed protein | 1.8 | 689.4 | P | 2484 | P |
| At3g44350 | No apical meristem (NAM) protein family | 1.8 | 85 | A | 367.3 | P |
| At3g49530 | No apical meristem (NAM) protein family | 1.8 | 780 | P | 2858 | P |
| At5g47230 | ethylene responsive element binding factor 5 (AtERF5) | 1.8 | 272.1 | P | 801 | P |
| At5g54720 | hypothetical protein | 1.8 | 370 | P | 1150 | P |
| At5g61900 | copine BONZAI1 (BON1) | 1.8 | 448.8 | P | 1797 | P |
| At2g41100 | calmodulin-related protein 3, touch-induced (TCH3) | 1.7 | 4135 | P | 10889 | P |
| At2g25735 | expressed protein | 1.7 | 129.1 | P | 533.8 | P |
| At2g32210 | expressed protein | 1.7 | 2023 | P | 6493 | P |
| At1g16420 | hypothetical protein common family | 1.7 | 161.2 | P | 473.7 | P |
| At1g72900 | disease resistance protein (TIR-NBS class), putative | 1.7 | 371.7 | P | 1186 | P |
| At1g80840 | WRKY family transcription factor | 1.7 | 683.5 | P | 2491 | P |
| At1g14370 | protein kinase (APK2a) | 1.7 | 302.4 | P | 1074 | P |
| At1g73805 | calmodulin-binding protein | 1.7 | 611.6 | P | 2495 | P |
| At3g28850 | expressed protein | 1.7 | 165.4 | P | 476.9 | P |
| At4g05110 | equilibrative nucleoside transporter ENT6 - related | 1.7 | 50.6 | A | 141.7 | P |
| At3g52430 | phytoalexin-deficient 4 protein (pad4) | 1.7 | 969.9 | P | 3082 | P |
| At5g24110 | WRKY family transcription factor | 1.7 | 60.5 | A | 294.7 | P |
| At5g58120 | disease resistance protein (TIR-NBS-LRR class), putative | 1.7 | 265.7 | P | 909.8 | P |
| At5g66210 | calcium-dependent protein kinase | 1.7 | 436.3 | P | 1675 | P |
| At5g14930 | leaf senescence-associated protein (SAG101) | 1.7 | 158 | P | 532.4 | P |
| At2g41640 | expressed protein | 1.7 | 433.9 | P | 1227 | P |
| At2g39650 | expressed protein | 1.6 | 293.7 | P | 955.8 | P |
| At2g41010 | expressed protein | 1.6 | 247.9 | P | 798.8 | P |
| At2g24800 | peroxidase, putative | 1.6 | 22.1 | A | 72.7 | P |
| At1g19020 | expressed protein | 1.6 | 2219.9 | P | 6688 | P |
| At3g14700 | expressed protein | 1.6 | 19.7 | A | 82.7 | P |
| At3g22930 | calmodulin, putative | 1.6 | 125.3 | P | 413.4 | P |
| At3g28340 | galactinol synthase, putative | 1.6 | 829.5 | P | 2880 | P |
| At1g51700 | Dof zinc finger protein | 1.6 | 671.2 | P | 1765 | P |
| At1g20823 | RING zinc finger protein-related | 1.6 | 158.6 | P | 503.8 | P |
| At4g12720 | MutT/nudix family protein | 1.6 | 4858 | P | 12878 | P |
| At4g18950 | protein kinase - like protein | 1.6 | 396.8 | P | 1145 | P |
| At4g23610 | expressed protein | 1.6 | 84.6 | P | 185.7 | P |
| At4g29740 | cytokinin oxidase family | 1.6 | 190.3 | P | 674.7 | P |
| At3g47540 | glycosyl hydrolase family 19 (chitinase) | 1.6 | 838.8 | P | 3223 | P |
| At3g48090 | disease resistance protein (EDS1) | 1.6 | 210.1 | P | 743.3 | P |
| At3g52400 | syntaxin of plants SYP122 | 1.6 | 1212.9 | P | 3891 | P |
| At3g54150 | embryonic abundant protein - related | 1.6 | 249.9 | P | 907.9 | P |
| At3g55150 | exocyst subunit EXO70 family | 1.6 | 104.9 | P | 380.1 | P |
| At5g10695 | expressed protein | 1.6 | 1242.9 | P | 3316 | P |
| At1g73540 | MutT/nudix family protein | 1.6 | 196.2 | P | 819.3 | P |
| At3g02800 | expressed protein | 1.6 | 135 | P | 207.3 | P |

TABLE 2

Changes of gene expression in hos9-1, genes with lower expression in hos9-1 by 2-fold

| AGI ID | Gene Title | hos9-1_vs_C24_0C-24H_ Signal Log Ratio | C24-0C-24H_ Signal | C24-0C-24H_ Detection | hos9-1_0C-24H_ Signal | hos9-1_0C-24H_ Detection |
|---|---|---|---|---|---|---|
| At1g75830 | plant defensin protein, putative (PDF1.1) | −2.3 | 120 | P | 29.8 | A |
| At3g28220 | expressed protein | −2.3 | 1423.8 | P | 320.5 | P |
| At5g44120 | 12S seed storage protein (CRA1) | −1.9 | 436.1 | P | 122.1 | P |
| At3g55970 | oxidoreductase, 2OG-Fe(II) oxygenase family | −1.8 | 290.7 | P | 92.6 | A |
| At1g60590 | polygalacturonase, putative | −1.7 | 523.1 | P | 146.5 | P |
| At5g44420 | plant defensin protein, putative (PDF1.2a) | −1.7 | 5058.4 | P | 1292.8 | P |
| At5g40420 | oleosin | −1.6 | 195.9 | P | 57.8 | A |
| At2g41260 | glycine-rich, late embryogenesis abundant M 17 protein | −1.5 | 102.5 | P | 39.3 | A |
| At2g21210 | auxin-induced (indole-3-acetic acid induced) protein, putative | −1.5 | 475.9 | P | 173.6 | A |
| At4g34760 | auxin-induced (indole-3-acetic acid induced) protein family | −1.5 | 201.6 | P | 75.1 | A |
| At5g57180 | CIA2 (CIA2) | −1.5 | 900.1 | P | 297.2 | P |
| At1g19670 | coronatine-induced protein 1 (CORI1) | −1.3 | 722 | P | 318.9 | P |
| At4g38860 | auxin-induced (indole-3-acetic acid induced) protein, putative | −1.3 | 228.5 | P | 82.8 | P |
| At5g03350 | expressed protein | −1.3 | 229.1 | P | 77 | A |
| At2g26020 | plant defensin protein, putative (PDF1.2b) | −1.3 | 14437 | P | 5323.6 | P |
| At2g39030 | GCN5-related N-acetyltransferase (GNAT) family | −1.2 | 1850.3 | P | 921.2 | P |
| At2g28200 | zinc-finger protein-related | −1.2 | 274.9 | P | 107 | P |
| At1g78995 | expressed protein | −1.2 | 452.9 | P | 164.7 | A |

TABLE 2-continued

Changes of gene expression in hos9-1, genes with lower expression in hos9-1 by 2-fold

| AGI ID | Gene Title | hos9-1_ vs_C24_0C-24H_ Signal Log Ratio | C24-0C-24H_ Signal | C24-0C-24H_ Detection | hos9-1_0C-24H_ Signal | hos9-1_0C-24H_ Detection |
|---|---|---|---|---|---|---|
| At1g19960 | expressed protein | −1.2 | 883 | P | 362.4 | P |
| At4g26150 | GATA zinc finger protein | −1.2 | 1173.2 | P | 504.4 | P |
| At1g70700 | expressed protein | −1.1 | 1102.4 | P | 676.9 | P |
| At4g25990 | CIL protein | −1.1 | 255.8 | P | 114.3 | P |
| At4g28520 | 12S seed storage protein (cruciferin), putative | −1.1 | 445.1 | P | 132.5 | P |
| At3g49620 | oxidoreductase (din11), putative | −1.1 | 1752.3 | P | 854 | P |
| At5g63530 | copper chaperone (CCH)-related | −1.1 | 355.3 | P | 151.9 | P |
| At2g38240 | oxidoreductase, 2OG-Fe(II) oxygenase family | −1 | 602.8 | P | 293.8 | M |
| At2g28410 | predicted GPI-anchored protein | −1 | 109.4 | P | 83.9 | A |
| At1g10640 | polygalacturonase, putative | −1 | 183.8 | P | 98.3 | A |
| At1g06160 | ethylene response factor, putative | −1 | 141.2 | P | 78.8 | A |
| At1g52400 | glycosyl hydrolase family 1, beta-glucosidase (BG1) | −1 | 3821.8 | P | 1705.9 | P |
| At3g03190 | glutathione transferase, putative | −1 | 239 | P | 139.3 | A |
| At3g15095 | hypothetical protein | −1 | 341.2 | P | 158 | P |
| At1g51780 | auxin conjugate hydrolase/IAA-amino acid hydrolase (ILL5) | −1 | 315.6 | P | 180.3 | P |
| At4g12970 | expressed protein | −1 | 249.6 | P | 119.5 | A |
| At5g05600 | oxidoreductase, 2OG-Fe(II) oxygenase family | −1 | 1022.4 | P | 526.7 | P |

TABLE 3

Changes of gene expression in hos9-1, genes with higher expression in hos9-1 by 3-fold but that are also cold-inducible

| AGI ID | Gene Title | hos9-1_ vs_C24_0C-24H_ Signal Log Ratio | C24-0C-24H_ Signal | C24-0C-24H_ Detection | hos9-1_0C-24H_ Signal | hos9-1_0C-24H_ Detection |
|---|---|---|---|---|---|---|
| At5g51190 | AP2 domain transcription factor, putative | 3.5 | 89.7 | P | 899.4 | P |
| At3g55840 | nematode resistance protein-related protein | 3.1 | 242.3 | P | 2235.7 | P |
| At1g15010 | expressed protein | 2.7 | 242.4 | P | 1691.8 | P |
| At4g24570 | mitochondrial carrier protein family | 2.7 | 631.6 | P | 4457.9 | P |
| At3g55980 | expressed protein | 2.7 | 569.8 | P | 3893.9 | P |
| At5g54490 | calcium-binding protein, putative | 2.7 | 585 | P | 4119.6 | P |
| At5g64870 | nodulin-related | 2.7 | 161.1 | P | 993.2 | P |
| At2g46400 | WRKY family transcription factor | 2.6 | 892.4 | P | 4361.3 | P |
| At4g17490 | ethylene responsive element binding factor (ERF6) | 2.6 | 65.2 | A | 461.7 | P |
| At1g28370 | ethylene responsive element binding factor 11, (EREBP11/ERF11) | 2.5 | 365.6 | P | 2024.4 | P |
| At1g61340 | F-box protein family | 2.4 | 363.3 | A | 2327.3 | P |
| At5g26920 | calmodulin-binding protein | 2.4 | 1241.8 | P | 6901.1 | P |
| At2g35710 | glycogenin glucosyltransferase (glycogenin) - related | 2.3 | 162 | P | 1079.8 | P |
| At3g10930 | expressed protein | 2.3 | 130.8 | P | 611 | P |
| At3g50930 | AAA-type ATPase family | 2.3 | 1016.2 | P | 5180.2 | P |
| At5g42380 | calmodulin-related protein, putative | 2.3 | 468.2 | P | 1878.4 | P |
| At5g45630 | hypothetical protein | 2.3 | 108.5 | P | 490.8 | P |
| At3g22910 | calcium-transporting ATPase (calcium pump), putative | 2.2 | 1152.9 | P | 5720.2 | P |
| At4g29780 | expressed protein | 2.1 | 518.2 | P | 2529.9 | P |
| At4g39670 | expressed protein | 2.1 | 900.3 | P | 4211.8 | P |
| At1g21110 | O-methyltransferase 1, putative | 2 | 111.4 | P | 461.7 | P |
| At2g38470 | WRKY family transcription factor | 1.9 | 1705.6 | P | 6281.5 | P |
| At2g30020 | protein phosphatase 2C (PP2C), putative | 1.9 | 165.5 | P | 587.6 | P |
| At1g76650 | calcium-binding EF-hand family protein | 1.9 | 154.3 | P | 562.4 | P |
| At3g02840 | expressed protein | 1.9 | 164 | P | 788.6 | P |
| At4g27280 | calcium-binding EF-hand family protein | 1.9 | 3174.7 | P | 11729 | P |
| At3g44260 | CCR4-associated factor 1-related protein | 1.9 | 138.9 | P | 510.5 | P |
| At3g61190 | BON1-associated protein 1 (BAP1) | 1.9 | 1221.4 | P | 5343.4 | P |
| At3g56880 | expressed protein | 1.9 | 2060.1 | P | 7606.7 | P |
| At2g32190 | expressed protein | 1.8 | 1051.7 | P | 3317.8 | P |
| At1g72520 | lipoxygenase (LOX), putative | 1.8 | 301.6 | P | 1055.6 | P |
| At5g47230 | ethylene responsive element binding factor 5 (AtERF5) | 1.8 | 272.1 | P | 801 | P |
| At2g32210 | expressed protein | 1.7 | 2023 | P | 6492.9 | P |
| At1g80840 | WRKY family transcription factor | 1.7 | 683.5 | P | 2490.8 | P |
| At2g41640 | expressed protein | 1.7 | 433.9 | P | 1227.3 | P |
| At2g41010 | expressed protein | 1.6 | 247.9 | P | 798.8 | P |
| At1g19020 | expressed protein | 1.6 | 2219.9 | P | 6687.5 | P |
| At3g28340 | galactinol synthase, putative | 1.6 | 829.5 | P | 2879.7 | P |

TABLE 3-continued

Changes of gene expression in hos9-1, genes with higher expression in hos9-1 by 3-fold but that are also cold-inducible

| AGI ID | Gene Title | hos9-1_vs_C24_0C-24H_Signal Log Ratio | C24-0C-24H_Signal | C24-0C-24H_Detection | hos9-1_0C-24H_Signal | hos9-1_0C-24H_Detection |
|---|---|---|---|---|---|---|
| At3g52400 | syntaxin of plants SYP122 | 1.6 | 1212.9 | P | 3891.1 | P |
| At5g10695 | expressed protein | 1.6 | 1242.9 | P | 3316.3 | P |
| At1g73540 | MutT/nudix family protein | 1.6 | 196.2 | P | 819.3 | P |

Materials And Methods
HOS9 nucleic acid sequence

```
  1 ATGGGCTACA TCTCCAACAA CAACCTCATC AACTATTTGC CCCTCTCTAC TACTCAACCT  (SEQ ID NO: 1)

61 CCTCTTCTTC TCACCCACTG TAATAAAATC CTTACTTCTT CATTTATAGA CTTAATTCAT

121 ATCAATGTGT TAATATTTTT GTTTTTTTCA GGTGATATTA ACGGCAATGA TCACCATCAG

181 CTCATAACCG CATCATCAGG AGAACACGAT ATTGATGAAC GGAAAAACAA CATTCCTGCG

241 GCGGCGACTT TGAGATGGAA TCCGACGCCA GAGCAGATCA CGACGCTAGA AGAGCTTTAC

301 AGAAGCGGAA CACGGACGCC GACGACGGAA CAGATCCAAC AGATAGCATC TAAGCTTCGT

361 AAATATGGGA GAATCGAAGG GAAGAACGTT TTCTATTGGT TTCAGAATCA TAAGGCTAGA

421 GAGAGACTAA AACGCCGCCG TCGTGAAGGT GGTGCTATTA TCAAACCACA TAAAGACGTC

481 AAGGATTCAT CATCAGGTGG TCATCGAGTT GATCAGACAA AGCTCTGCCC ATCTTTTCCA

541 CACACAAACC GACCACAGCC ACAGCATGAA TTAGATCCTG CGAGTTACAA TAAAGACAAC

601 AATGCTAATA ATGAAGATCA TGGGACGACT GAAGAATCTG ATCAGAGGGC ATCAGAGGTT

661 GGTAAATACG CCACATGGAG AAATCTTGTT ACTTGGTCGA TAACTCAACA ACCGGAAGAG

721 ATTAATATCG ACGAAAATGT CAACGGAGAA GAAGAAGAAA CGAGGGACAA CCGGACTTTA

781 AATCTCTTTC CGGTTAGGGA GTACCAAGAG AAAACAGGCC GGTTGATAGA GAAGACGAAA

841 GCATGCAACT ACTGTTACTA CTACGAGTTC ATGCCTCTGA AGAACTGA
```

HOS9 amino acid sequence

```
MGYISNNNLI NYLPLSTTQP PLLLTHCNKI LTSSFIDLIH INVLIFLFFS  (SEQ ID NO: 2)

GDINGNDKHQ LITASSGEHD IDERKNNIPA AATLRWNPTP EQITTLEELY

RSGTRTPTTE QIQQIASKLR KYGRIEGKNV FYWFQNHKAR ERLKRRRREG

GAIIKPHKDV KDSSSGGHRV DQTKLCPSFP HTNRPQPQHE LDPASYNKDN

NANNEDHGTT EESDQRASEV GKYATWRNLV TWSITQQPEE INIDENVNGE

EEETRDNRTL NLFPVREYQE KTGRLIEKTK ACNYCYYYEF MPLKN
```

Plant Materials. *Arabidopsis thaliana* plants (ecotype C24) expressing the homozygous transgene RD29A::LUC (referred to as wild type) were mutagenized with an *Agrobacterium tumefaciens*-mediated (strain GV3101) T-DNA transformation (Ishitani et al., (1997) Plant Cell 9, 1935–1949; Zhu et al., (2002) Plant Cell 14, 3009–3028). Seeds from T2 plants were used for screening mutants that exhibited altered expression of RD29A::LUC in response to cold, ABA, and/or osmotic stress by luminescence imaging by using a charge-coupled device camera, as described (Ishitani et al., (1997)).

Freezing Tolerance. Three-week-old hos9-1 and wild-type plants were grown in soil at room temperature or at 4° C. under a long-day photoperiod (16 h light/8 h dark) for 1 week. Fully developed rosette leaves were used for electrolyte leakage measurements, as described (Sukumaran &

Weiser (1972) Hort. Sci. 7, 467–468; Ristic & Ashworth (1993) Protoplasma 172, 111–123; Guo et al.,. (2002) Proc. Natl. Acad. Sci. USA 99, 7786–7791).

Whole-plant freezing tests were as described (Xiong et al., (2001) Plant Cell 13, 2063–2083) with modifications. Wild-type and hos9-1 plants were grown in soil in a growth chamber (23±2° C.), under a long-day photoperiod (16 h light/8 h dark) or short-day photoperiod (8 h light/16 h dark) for 3 weeks and then incubated at 4° C. for 1 week for cold acclimation under either long- or short-day photoperiods. The plants were then placed in a temperature chamber (model Tenney-JR, Tenney Engineering, Garland, Tex.) with the following freezing temperature regimen: from 4° C. to −2° C. in 30 min, then hold at −2° C. for 1 h; then an identical timing sequence (30 min to reach the next temperature, hold there for 1 h) for successive 2° C. decreases until −12° C. was reached. Plants damage was scored 7 d later (Xiong et al., (2001)).

Northern Blot and Microarray Analyses. Wild-type and hos9-1 seedlings were grown on separate halves of the same Murashige and Skoog (Murashige & Skoog (1962) Physiol. Plant 15, 473–497) agar plates for 14 d and then left untreated or treated with low temperature, ABA, or NaCl. Total RNA was extracted from whole seedlings, and RNA analysis was conducted as described (27). Gene specific probes for RD29A, Actin, FLC, CBF1, CBF2, CBF3, and -tubulin were as described (Ishitani et al., (1998) Plant Cell 10, 1151–1161; Lee et al., (2001) Genes Dev. 15, 912–924; Lee et al., (2002) Plant Cell 14, 1235–1251).

Total RNA (20 μl) extracted with the RNeasy Plant Mini Kit (Qiagen, Valencia, Calif.) from 21-d-old wild-type and hos9-1 seedlings after cold treatment (24 h at 0° C.) was used to make biotin-labeled cRNA targets. Microarray analysis (Affymetrix GeneChip array) was performed as described (Chinnusamy et al., (2003) Genes Dev. 17, 1043–1054).

Cloning of the HOS9 Gene. The genomic DNA fragment flanking the left border of the inserted T-DNA in hos9-1 plants was isolated by thermal asymmetric interlaced PCR, as described (Zhu et al., (2002) Plant Cell 14, 3009–3028; Liu et al., (1995) Plant J. 8, 457–463). The following primer pair was designed to perform the T-DNA diagnosis PCR: forward, 5'-TACTTCTGAGGTACTTTATTAGGTGAC-3' (SEQ ID NO: 3); reverse, 5'-TCAACGTGGACATAC-CATTTAAAG-3 ' (SEQ ID NO: 4)(Zhu et al., (2002)). To estimate the functional T-DNA copy number in the hos9-1 mutant genome, the following primers, for the basta gene were used, 5'-AAACCCACGTCATGCCAGTTC-3' (SEQ ID NO: 5) and 5'-CCATCGTCAACCACTACATCGAGAC-3' (SEQ ID NO: 6).

A genomic fragment that includes the putative HOS9 gene including 1,457 bp upstream of the initiation codon and 556 bp downstream of the stop codon from bacterial artificial chromosome (BAC) clone F2I9 was amplified by PCR. The PCR fragment was cloned into the binary vector pCAMBIA1200 (CAMBIA, Black Mountain, Australia) between the KpnI and PstI sites and the identity of the clone insert was confirmed by sequencing. The construct was introduced into hos9-1 mutant plants through an *A. tumefaciens*-mediated (strain GV3101) T-DNA transformation. Primary transformants were isolated on Murashige and Skoog medium containing 50 mg/l hygromycin (Invitrogen) and transferred to soil to grow to maturity. Progenies of these transformants were examined for RD29A::LUC expression with the charge-coupled device camera and for freezing tolerance in the temperature chamber as described above.

RT-PCR Analysis. Total RNA (3 μg) was extracted from plant tissues by using the RNeasy Plant Mini Kit and used for first-strand cDNA synthesis using therinoscript RT-PCR system (Invitrogen). PCR amplifications for HOS9 were performed by using PfuTurbo DNA polymerase (Stratagene) following the manufacturer's instructions. The gene specific primers for HOS9 were as follows: forward primer, 5'-ATGGGCTACATCTCCAACAACAAC-3' (SEQ ID NO: 7); and reverse primer, 5'-TCAGTTCTTCAGAGGCAT-GAACTC-3' (SEQ ID NO: 8). Gene-specific primers for RD29A, Tubulin and Actin were as described (Ishitani et al., (1998); Lee et al., (2001)). The RT-PCR product amplified from nontreated wild-type plants was subcloned into the pGEM-T Easy Vector with (Promega). The resulting 9-22 clone and the sequence of the insert were confirmed by sequencing. Gene-specific primers used to confirm the microarray results were as follow: At2g46400-F, 5'-TGAAT-GCAAAGATGATGG-3' (SEQ ID NO: 9) and At2g46400-R, 5'-TTGCCCATATTTTCTCCAGCAG-3' (SEQ ID NO: 10) for At2g46400; At2g32210-F, 5'-TCCTACGCCGC-CAGTGTCTAC-3' (SEQ ID NO: 11) and At2g32210-R, 5'-GTCCACGTTGACTAACCGGT-3' (SEQ ID NO: 12) for At2g32210; At5g44420-F, 5' -TGGCTAAGTTTGCTTC-CATCATC-31 ' (SEQ ID NO: 13) and At5g44420-R, 5' -CAACGGGAAAATAAACATTAAAAC-3' (SEQ ID NO: 14) for At5g44420.

Analysis of HOS9 Promoter::GUS Expression. A genomic fragment including 1,457 bp upstream of the initiation codon from BAC clone F2I9 that was used for the gene complementation test was amplified by PCR and cloned into the binary vector pCAMBIA1381Z (CAMBIA) between the BamHI and HindIII sites. The identity of the cloned insert was confirmed by sequencing. *A. tumefaciens* strain GV3101 containing this construct was used to transform *Arabidopsis* Columbia wild-type plants. To measure—glucuronidase (GUS) activity, tissues from transgenic plants were incubated overnight at 37° C. in the dark, in 1 mM 5-bromo-4-chloro-3-indolyl—D-glucuronide (Rose Scientific, Cincinnati) and 0.1 M potassium phosphate buffer (pH 7.5) with 0.1% Triton X-100 (31). Chlorophyll was removed by washing several times with 70% ethanol.

GFP-HOS9 Fusion Protein Construct. The HOS9 coding region was amplified by PCR and cloned in-frame into pGEAD vector between the EcoRI and BamHI sites and the entire insert and the conjunction regions were sequenced. This construct was then introduced into *Arabidopsis* wild-type plants (ecotype Columbia) by using floral dip transformation with *Agrobacterium* strain GV3101.

Cytosolic Free Ca2+ Measurement. Lines expressing 35S::Aequorin (Knight et al., (1991) Nature 352, 524–526) were crossed with the hos9-1 mutant. F2 plants from the cross homozygous for the hos9-1 mutation and for the Aequorin gene were selected by PCR analysis. The 35S::Aequorin expressing line was also crossed with HOS9 wild-type plants (C24 with RD29A::LUC). F2 plants homozygous for the Aequorin transgene were selected by PCR analysis and used for controls. To determine the cytosolic free Ca2+, Aequorin-dependent luminescence from 8-day-old seedlings grown on agar plates was measured with a charge-coupled device camera, as described (Knight et al., (1999) Plant Cell 11, 875–886; Ishitani et al., (1997)).

Transformation methods. Methods for specifically transforming dicots use *Agrobacterium tumefaciens*. For example, transgenic plants reported include but are not limited to cotton (U.S. Pat. Nos. 5,004,863; 5,159,135; 5,518,908, WO 97/43430), soybean (U.S. Pat. Nos. 5,569, 834; 5,416,011; McCabe et al., Bio/Technology, 6:923, 1988; Christou et al., Plant Physiol., 87:671, 1988); Brassica (U.S. Pat. No. 5,463,174), and peanut (Cheng et al., Plant Cell Rep., 15:653, 1996).

Similar methods have been reported in the transformation of monocots. Various monocot transformation vectors using *Agrobacterium*-mediated transformation are available (Wang et al., 1998. Improved vectors for *Agrobacterium tumefaciens*-mediated transformation of monocot plants. Acta Hort. 461:401–408; Schünmann et al., 2003; A suite of novel promoters and terminators for plant biotechnology. II. The pPLEX series for use in monocots. Functional Plant Biology 30(4) 453–460). Transformation and plant regeneration using these methods have been described for a number of crops including but not limited to asparagus (Asparagus officinalis; Bytebier et al., Proc. Natl. Acad. Sci. U.S.A., 84:5345, 1987); barley (*Hordeum vulgarae;* Wan and Lemaux, Plant Physiol., 104:37, 1994); maize (*Zea mays;* Rhodes, C. A., et al., Science, 240:204, 1988; Gordon-Kamm, et al., Plant Cell, 2:603, 1990; Fromm, et al., Bio/Technology, 8:833, 1990; Koziel, et al., Bio/Technology, 11: 194, 1993); oats (*Avena sativa;* Somers, et al., Bio/Technology, 10:1589, 1992); orchardgrass (*Dactylis glomerata;* Horn, et al., Plant Cell Rep., 7:469, 1988); rice (*Oryza sativa,* including *indica* and *japonica* varieties, Toriyama, et al., Bio/Technology, 6:10, 1988; Zhang, et al., Plant Cell Rep., 7:379, 1988; Luo and Wu, Plant Mol. Biol. Rep., 6:165, 1988; Zhang and Wu, Theor. Appl. Genet., 76:835, 1988; Christou, et al., Bio/Technology, 9:957, 1991); sorghum (*Sorghum bicolor;* Casas, A. M., et al., Proc. Natl. Acad. Sci. U.S.A., 90:11212, 1993); sugar cane (*Saccharum* spp.; Bower and Birch, Plant J., 2:409, 1992); tall fescue (*Festuca arundinacea;* Wang, Z. Y. et al., Bio/Technology, 10:691, 1992); turfgrass (*Agrostis palustris;* Zhong et al., Plant Cell Rep., 13:1, 1993); wheat (*Triticum aestivum;* Vasil et al., Bio/Technology, 10:667, 1992; Weeks T., et al., Plant Physiol., 102:1077, 1993; Becker, et al., Plant, J. 5:299, 1994), and alfalfa (Masoud, S. A., et al., Transgen. Res., 5:313, 1996). It is apparent to those of skill in the art that a number of transformation methodologies can be used and modified for production of stable transgenic plants from any number of target crops of interest.

The U.S. patents mentioned in this disclosure are herein incorporated by reference to the extent they relate to materials and methods disclosed herein.

We claim:

1. A method of producing a transgenic plant comprising a nucleic acid molecule encoding the polypeptide as set forth in SEQ ID NO: 2, the method comprising:
   (a) transforming a plant cell with an expression vector comprising a promoter functional in a plant cell operably linked to an isolated nucleic acid molecule encoding SEQ ID NO: 2, wherein expression of the nucleic acid molecule in a plant cell results in the plant cell's increased tolerance to an environmental stress as compared to a wild-type plant cell, and wherein the environmental stress is selected from the group consisting of cold temperature and freezing temperature; and
   (b) obtaining a transgenic plant from the plant cell that expresses the polypeptide.

2. A transgenic plant transformed with a nucleic acid molecule encoding a polypeptide as set forth in SEQ ID NO: 2, wherein an increased level of expression of the polypeptide improves cold tolerance to the transgenic plant compared to a wild-type plant.

3. A seed produced by the plant of claim 2, wherein the seed comprises a nucleic acid molecule comprising the sequence set forth in SEQ ID NO: 1.

4. A transgenic plant cell comprising a nucleic acid sequence as set forth in SEQ ID NO: 1, operably linked to a promoter, wherein expression of the nucleic acid molecule confers increased cold tolerance as compared to a wild-type plant cell.

* * * * *

SEQUENCE LISTING

<160> NUMBER OF SEQ ID NOS: 17

<210> SEQ ID NO 1
<211> LENGTH: 888
<212> TYPE: DNA
<213> ORGANISM: Arabidopsis thaliana

<400> SEQUENCE: 1

```
atgggctaca tctccaacaa caacctcatc aactatttgc ccctctctac tactcaacct      60
cctcttcttc tcacccactg taataaaatc cttacttctt catttataga cttaattcat     120
atcaatgtgt taatatttt gttttttca ggtgatatta acggcaatga tcaccatcag     180
ctcataaccg catcatcagg agaacacgat attgatgaac ggaaaaacaa cattcctgcg     240
gcggcgactt tgagatggaa tccgacgcca gagcagatca cgacgctaga agagctttac     300
agaagcggaa cacggacgcc gacgacggaa cagatccaac agatagcatc taagcttcgt     360
aaatatggga gaatcgaagg gaagaacgtt ttctattggt ttcagaatca taaggctaga     420
gagagactaa aacgccgccg tcgtgaaggt ggtgctatta tcaaaccaca taaagacgtc     480
aaggattcat catcaggtgg tcatcgagtt gatcagacaa agctctgccc atcttttcca     540
cacacaaacc gaccacagcc acagcatgaa ttagatcctg cgagttacaa taaagacaac     600
aatgctaata atgaagatca tgggacgact gaagaatctg atcagagggc atcagaggtt     660
ggtaaatacg ccacatggag aaatcttgtt acttggtcga taactcaaca accggaagag     720
attaatatcg acgaaaatgt caacggagaa gaagaagaaa cgagggacaa ccggacttta     780
aatctctttc cggttaggga gtaccaagag aaaacaggcc ggttgataga gaagacgaaa     840
gcatgcaact actgttacta ctacgagttc atgcctctga agaactga               888
```

<210> SEQ ID NO 2
<211> LENGTH: 295
<212> TYPE: PRT
<213> ORGANISM: Arabidopsis thaliana

<400> SEQUENCE: 2

```
Met Gly Tyr Ile Ser Asn Asn Asn Leu Ile Asn Tyr Leu Pro Leu Ser
 1               5                  10                  15

Thr Thr Gln Pro Pro Leu Leu Thr His Cys Asn Lys Ile Leu Thr
             20                  25                  30

Ser Ser Phe Ile Asp Leu Ile His Ile Asn Val Leu Ile Phe Leu Phe
             35                  40                  45

Phe Ser Gly Asp Ile Asn Gly Asn Asp Lys His Gln Leu Ile Thr Ala
         50                  55                  60

Ser Ser Gly Glu His Asp Ile Asp Glu Arg Lys Asn Asn Ile Pro Ala
 65                  70                  75                  80

Ala Ala Thr Leu Arg Trp Asn Pro Thr Pro Glu Gln Ile Thr Thr Leu
             85                  90                  95

Glu Glu Leu Tyr Arg Ser Gly Thr Arg Thr Pro Thr Thr Glu Gln Ile
             100                 105                 110

Gln Gln Ile Ala Ser Lys Leu Arg Lys Tyr Gly Arg Ile Glu Gly Lys
             115                 120                 125

Asn Val Phe Tyr Trp Phe Gln Asn His Lys Ala Arg Glu Arg Leu Lys
 130                 135                 140

Arg Arg Arg Arg Glu Gly Gly Ala Ile Ile Lys Pro His Lys Asp Val
145                 150                 155                 160

Lys Asp Ser Ser Ser Gly Gly His Arg Val Asp Gln Thr Lys Leu Cys
             165                 170                 175

Pro Ser Phe Pro His Thr Asn Arg Pro Gln Pro Gln His Glu Leu Asp
             180                 185                 190

Pro Ala Ser Tyr Asn Lys Asp Asn Asn Ala Asn Asn Glu Asp His Gly
             195                 200                 205

Thr Thr Glu Glu Ser Asp Gln Arg Ala Ser Glu Val Gly Lys Tyr Ala
             210                 215                 220

Thr Trp Arg Asn Leu Val Thr Trp Ser Ile Thr Gln Gln Pro Glu Glu
225                 230                 235                 240

Ile Asn Ile Asp Glu Asn Val Asn Gly Glu Glu Glu Thr Arg Asp
                 245                 250                 255

Asn Arg Thr Leu Asn Leu Phe Pro Val Arg Glu Tyr Gln Glu Lys Thr
             260                 265                 270

Gly Arg Leu Ile Glu Lys Thr Lys Ala Cys Asn Tyr Cys Tyr Tyr Tyr
             275                 280                 285

Glu Phe Met Pro Leu Lys Asn
             290                 295

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tacttctgag gtactttatt aggtgac                                         27

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 4
tcaacgtgga cataccattt aaag                                      24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaacccacgt catgccagtt c                                         21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccatcgtcaa ccactacatc gagac                                     25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgggctaca tctccaacaa caac                                      24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcagttcttc agaggcatga actc                                      24

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgaatgcaaa gatgatgg                                             18

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 10
ttgcccatat tttctccagc ag                                              22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcctacgccg ccagtgtcta c                                               21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtccacgttg actaaccggt                                                 20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggctaagtt tgcttccatc atc                                             23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caacgggaaa ataaacatta aaac                                            24

<210> SEQ ID NO 15
<211> LENGTH: 236
<212> TYPE: PRT
<213> ORGANISM: Arabidopsis thaliana

<400> SEQUENCE: 15

Met Ser Pro Val Ala Ser Thr Arg Trp Cys Pro Thr Pro Glu Gln Leu
  1               5                  10                  15

Met Ile Leu Glu Glu Met Tyr Arg Ser Gly Ile Arg Thr Pro Asn Ala
                 20                  25                  30

Val Gln Ile Gln Gln Ile Thr Ala His Leu Ala Phe Tyr Gly Arg Ile
             35                  40                  45

Glu Gly Lys Asn Val Phe Tyr Trp Phe Gln Asn His Lys Ala Arg Asp
         50                  55                  60

Arg Gln Lys Leu Arg Lys Lys Leu Ala Lys Gln Leu His Gln Gln Gln
 65                  70                  75                  80
```

```
His Gln Leu Gln Leu Gln Leu Gln Gln Ile Lys Pro Lys Pro Ile Ser
             85                  90                  95

Ser Met Ile Ser Gln Pro Val Asn Lys Asn Ile Ile Asp His His Asn
            100                 105                 110

Pro Tyr His His His His Asn His His Asn His His Arg Pro
            115                 120                 125

Tyr Asp His Met Ser Phe Asp Cys Cys Ser His Pro Ser Pro Met Cys
130                 135                 140

Leu Pro His Gln Gly Thr Gly Val Gly Glu Ala Pro Ser Lys Val Met
145                 150                 155                 160

Asn Glu Tyr Tyr Cys Thr Lys Ser Gly Ala Glu Glu Ile Leu Met Gln
                165                 170                 175

Lys Ser Ile Thr Gly Pro Asn Ser Ser Tyr Gly Arg Asp Trp Met Met
            180                 185                 190

Met Met Asp Met Gly Pro Arg Pro Ser Tyr Pro Ser Ser Ser Ser Ser
            195                 200                 205

Pro Ile Ser Cys Cys Asn Met Met Met Ser Ser Pro Lys Ile Pro Leu
210                 215                 220

Lys Thr Leu Glu Leu Phe Pro Ile Ser Ser Ile Asn
225                 230                 235

<210> SEQ ID NO 16
<211> LENGTH: 276
<212> TYPE: PRT
<213> ORGANISM: Arabidopsis thaliana

<400> SEQUENCE: 16

Met Glu Pro Pro Gln His Gln His His His Gln Ala Asp Gln Glu
1               5                   10                  15

Ser Gly Asn Asn Asn Asn Lys Ser Gly Ser Gly Gly Tyr Thr Cys Arg
            20                  25                  30

Gln Thr Ser Thr Arg Trp Thr Pro Thr Thr Glu Gln Ile Lys Ile Leu
        35                  40                  45

Lys Glu Leu Tyr Tyr Asn Asn Ala Ile Arg Ser Pro Thr Ala Asp Gln
50                  55                  60

Ile Gln Lys Ile Thr Ala Arg Leu Arg Gln Phe Gly Lys Ile Glu Gly
65                  70                  75                  80

Lys Asn Val Phe Tyr Trp Phe Gln Asn His Lys Ala Arg Glu Arg Gln
                85                  90                  95

Lys Lys Arg Phe Asn Gly Thr Asn Met Thr Thr Pro Ser Ser Ser Pro
            100                 105                 110

Asn Ser Val Met Met Ala Ala Asn Asp His Tyr His Pro Leu Leu His
            115                 120                 125

His His Gly Val Pro Met Gln Arg Pro Ala Asn Ser Val Asn Val
130                 135                 140

Lys Leu Asn Gln Asp His His Leu Tyr His His Asn Lys Pro Tyr Pro
145                 150                 155                 160

Ser Phe Asn Asn Gly Asn Leu Asn His Ala Ser Ser Gly Thr Glu Cys
                165                 170                 175

Gly Val Val Asn Ala Ser Asn Gly Tyr Met Ser Ser His Val Tyr Gly
            180                 185                 190

Ser Met Glu Gln Asp Cys Ser Met Asn Tyr Asn Asn Val Gly Gly Gly
            195                 200                 205
```

```
Trp Ala Asn Met Asp His His Tyr Ser Ser Ala Pro Tyr Asn Phe Phe
        210                 215                 220

Asp Arg Ala Lys Pro Leu Phe Gly Leu Glu Gly His Gln Asp Glu Glu
225                 230                 235                 240

Glu Cys Gly Gly Asp Ala Tyr Leu Glu His Arg Thr Leu Pro Leu
                245                 250                 255

Phe Pro Met His Gly Glu Asp His Ile Asn Gly Ser Gly Ala Ile
            260                 265                 270

Trp Lys Tyr Gly
            275

<210> SEQ ID NO 17
<211> LENGTH: 271
<212> TYPE: PRT
<213> ORGANISM: Arabidopsis thaliana

<400> SEQUENCE: 17

Met Gly Tyr Ile Ser Asn Asn Leu Ile Asn Tyr Leu Pro Leu Ser
  1               5                  10                  15

Thr Thr Gln Pro Pro Leu Leu Leu Thr His Cys Asp Ile Asn Gly Asn
                20                  25                  30

Asp His His Gln Leu Ile Thr Ala Ser Ser Gly Glu His Asp Ile Asp
            35                  40                  45

Glu Arg Lys Asn Asn Ile Pro Ala Ala Ala Thr Leu Arg Trp Asn Pro
 50                  55                  60

Thr Pro Glu Gln Ile Thr Thr Leu Glu Glu Leu Tyr Arg Ser Gly Thr
 65                  70                  75                  80

Arg Thr Pro Thr Thr Glu Gln Ile Gln Gln Ile Ala Ser Lys Leu Arg
                85                  90                  95

Lys Tyr Gly Arg Ile Glu Gly Lys Asn Val Phe Tyr Trp Phe Gln Asn
                100                 105                 110

His Lys Ala Arg Glu Arg Leu Lys Arg Arg Arg Glu Gly Gly Ala
            115                 120                 125

Ile Ile Lys Pro His Lys Asp Val Lys Asp Ser Ser Ser Gly Gly His
            130                 135                 140

Arg Val Asp Gln Thr Lys Leu Cys Pro Ser Phe Pro His Thr Asn Arg
145                 150                 155                 160

Pro Gln Pro Gln His Glu Leu Asp Pro Ala Ser Tyr Asn Lys Asp Asn
                165                 170                 175

Asn Ala Asn Asn Glu Asp His Gly Thr Thr Glu Glu Ser Asp Gln Arg
            180                 185                 190

Ala Ser Glu Val Gly Lys Tyr Ala Thr Trp Arg Asn Leu Val Thr Trp
                195                 200                 205

Ser Ile Thr Gln Gln Pro Glu Glu Ile Asn Ile Asp Glu Asn Val Asn
            210                 215                 220

Gly Glu Glu Glu Glu Thr Arg Asp Asn Arg Thr Leu Asn Leu Phe Pro
225                 230                 235                 240

Val Arg Glu Tyr Gln Glu Lys Thr Gly Arg Leu Ile Glu Lys Thr Lys
                245                 250                 255

Ala Cys Asn Tyr Cys Tyr Tyr Glu Phe Met Pro Leu Lys Asn
                260                 265                 270
```